(12) United States Patent
Lou et al.

(10) Patent No.: US 10,172,660 B2
(45) Date of Patent: Jan. 8, 2019

(54) ASSEMBLY FOR DISPENSING BIOMATERIAL, PLUNGER THEREFOR, AND RELATED METHODS

(71) Applicant: Nordson Corporation, Westlake, OH (US)

(72) Inventors: Huadong Lou, Plymouth, MN (US); Bradley D. Robb, Maple Plain, MN (US); Zachary Rzeszutek, Minneapolis, MN (US); Mark Stevenson, Cottage Grove, MN (US)

(73) Assignee: Nordson Corporation, Westlake, OH (US)

( * ) Notice: Subject to any disclaimer, the term of this patent is extended or adjusted under 35 U.S.C. 154(b) by 1070 days.

(21) Appl. No.: 14/202,720

(22) Filed: Mar. 10, 2014

(65) Prior Publication Data

US 2014/0276581 A1    Sep. 18, 2014

Related U.S. Application Data

(60) Provisional application No. 61/778,839, filed on Mar. 13, 2013.

(51) Int. Cl.
  *A61B 17/88*      (2006.01)
(52) U.S. Cl.
  CPC .............................. *A61B 17/8822* (2013.01)
(58) Field of Classification Search
  CPC ...... A61F 2002/2817; A61F 2002/2835; A61F 2002/3008; A61F 2002/30581;
  (Continued)

(56) References Cited

U.S. PATENT DOCUMENTS

| | | | | |
|---|---|---|---|---|
| 5,512,054 A | * | 4/1996 | Morningstar | A61M 5/3129 604/191 |
| 6,045,555 A | | 4/2000 | Smith et al. | |

(Continued)

FOREIGN PATENT DOCUMENTS

| | | |
|---|---|---|
| EP | 1090610 | 4/2001 |
| WO | 9949818 A1 | 10/1999 |

(Continued)

OTHER PUBLICATIONS

European Application No. 14 159 527.2: EP First Office Action dated Oct. 5, 2016, 3 pages.

(Continued)

*Primary Examiner* — Brandy S Lee
(74) *Attorney, Agent, or Firm* — Baker & Hostetler LLP

(57) ABSTRACT

An assembly includes a dispensing syringe device configured to receive an amount of biomaterial and to dispense the biomaterial. The dispensing syringe device includes a syringe barrel for receiving the biomaterial, a discharge outlet for dispensing the biomaterial from the syringe barrel, and a plunger received in the syringe barrel. The plunger has a plunger body and a plunger passageway extending therethrough configured to receive a stylet. The assembly further includes a cannulus device configured to be coupled with the dispensing syringe device, to receive biomaterial from the dispensing syringe device, and to dispense the biomaterial. The cannulus device includes a cannulus passageway configured to receive the biomaterial and a dispensing opening configured for dispensing the biomaterial.

11 Claims, 20 Drawing Sheets

(58) Field of Classification Search
CPC .... A61F 2002/30677; A61F 2002/4602; A61F 2002/4623; A61F 2002/4624; A61F 2002/4635; A61F 2002/4662; A61F 2002/4685; A61M 2005/31598; A61M 5/3129; A61M 5/31505; A61M 5/31511; A61M 5/31596; A61M 2005/3121; A61M 2005/3128; A61M 2025/0063; A61M 2025/0175; A61M 25/0097; A61M 25/0102; A61M 25/0136; A61M 25/0606; A61M 5/142; A61M 5/14228; A61M 5/16836; A61B 17/8822; A61B 17/8827; A61B 17/8805; A61B 10/025; A61B 2017/8838; A61B 5/150236; A61B 5/150244

See application file for complete search history.

(56) References Cited

U.S. PATENT DOCUMENTS

| | | |
|---|---|---|
| 7,670,384 B2 | 3/2010 | Kumar et al. |
| 8,118,813 B2 | 2/2012 | Perez-Cruet et al. |
| 8,439,929 B1 | 5/2013 | Sharratt et al. |
| 2002/0099384 A1* | 7/2002 | Scribner ............ A61B 17/1631 606/92 |
| 2007/0010824 A1* | 1/2007 | Malandain ......... A61B 17/8822 606/92 |
| 2012/0330229 A1 | 12/2012 | Greter |

FOREIGN PATENT DOCUMENTS

| | | |
|---|---|---|
| WO | 2007008721 A1 | 1/2007 |
| WO | 2007048016 A2 | 4/2007 |
| WO | 2008153513 A2 | 12/2008 |
| WO | 2012066905 A1 | 5/2012 |

OTHER PUBLICATIONS

European Patent Office, Search Report in EP Application No. 14159527, dated Jun. 25, 2014.

Nordson Corporation, OsteoXpress™ Bone Graft Delivery, www.nordson.com/en-us/divisions/micromedics/products/bone-graft-delivery/pages/default.aspx, 1 pg., 2013.

Medmix Systems AG, Bone-Graft Delivery System, Brochure, 4 pgs., undated.

* cited by examiner

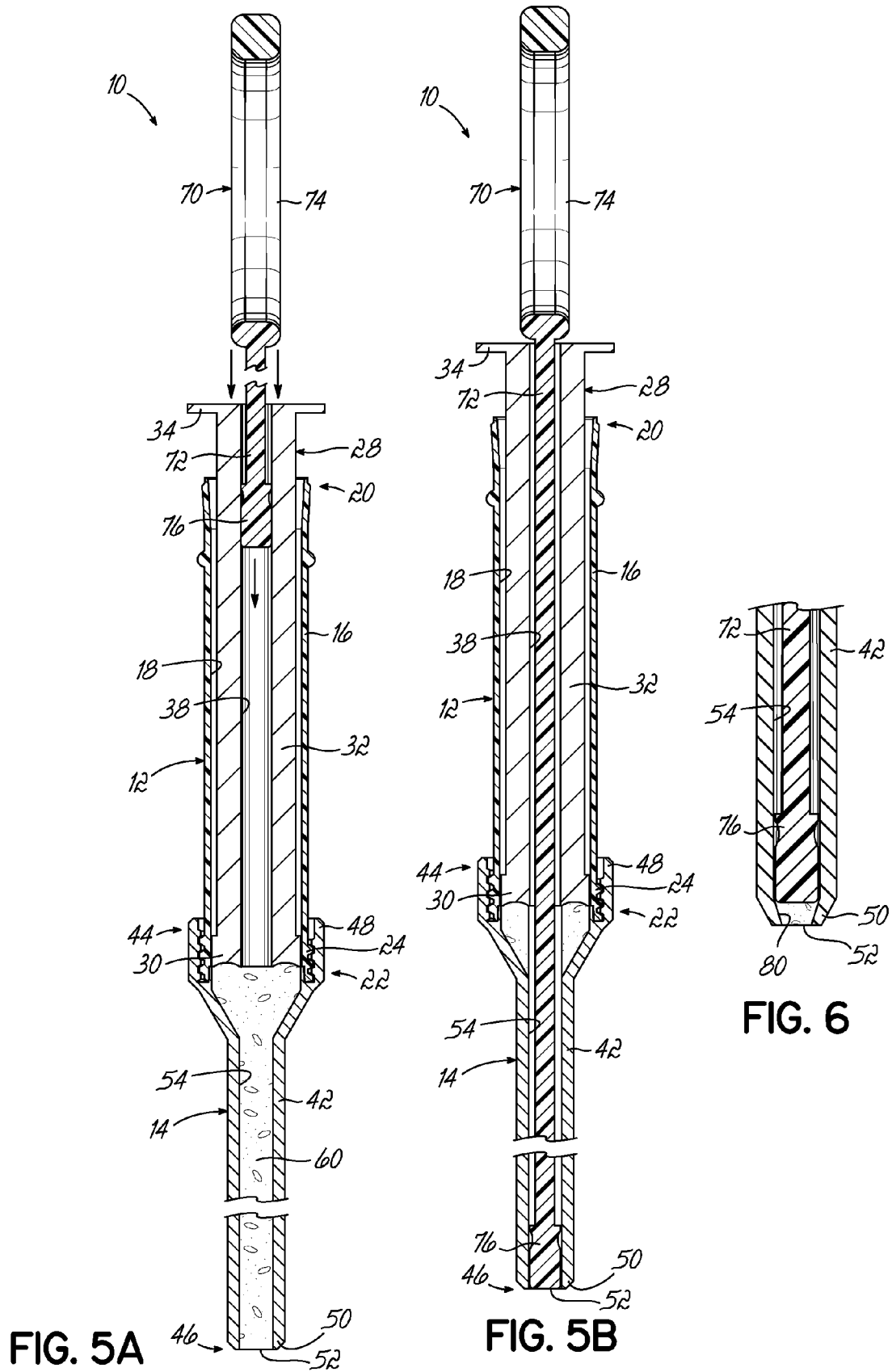

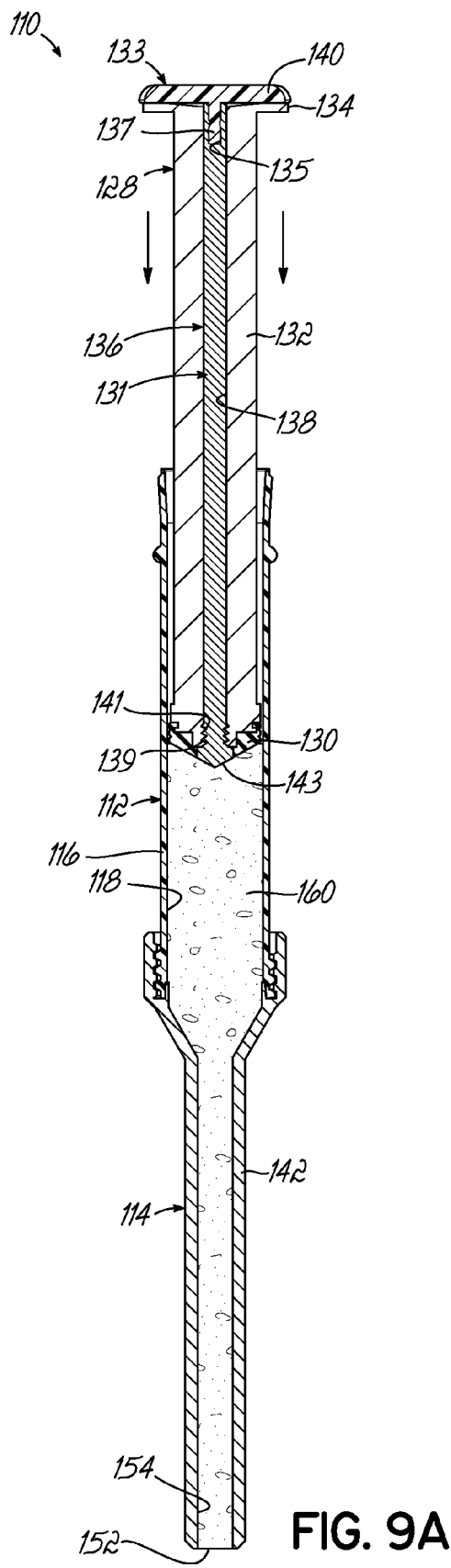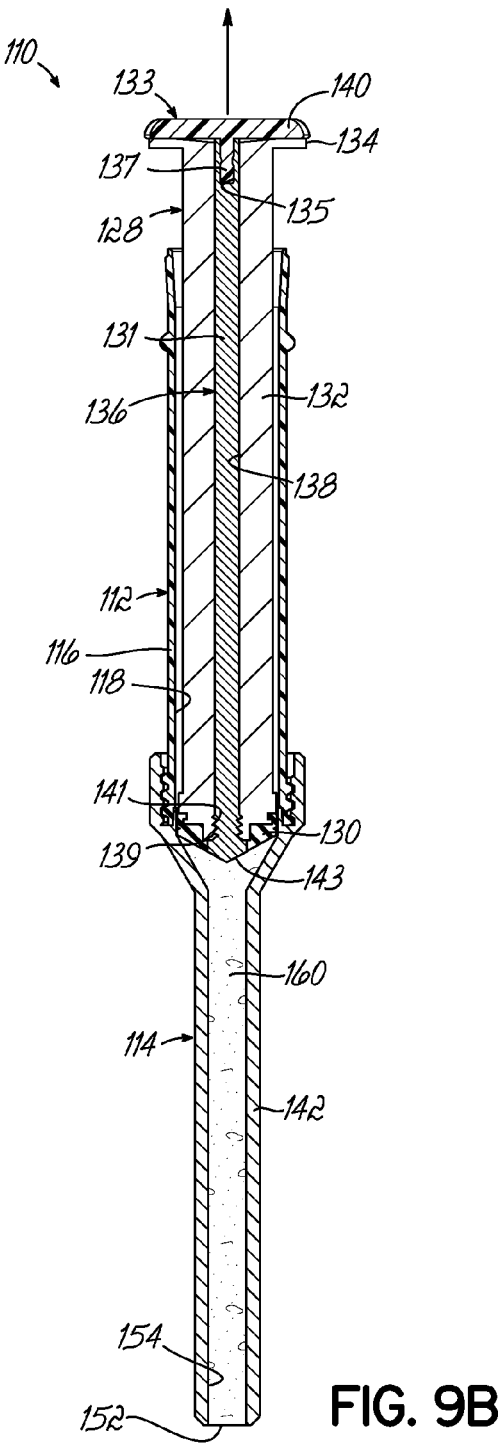
FIG. 9A
FIG. 9B

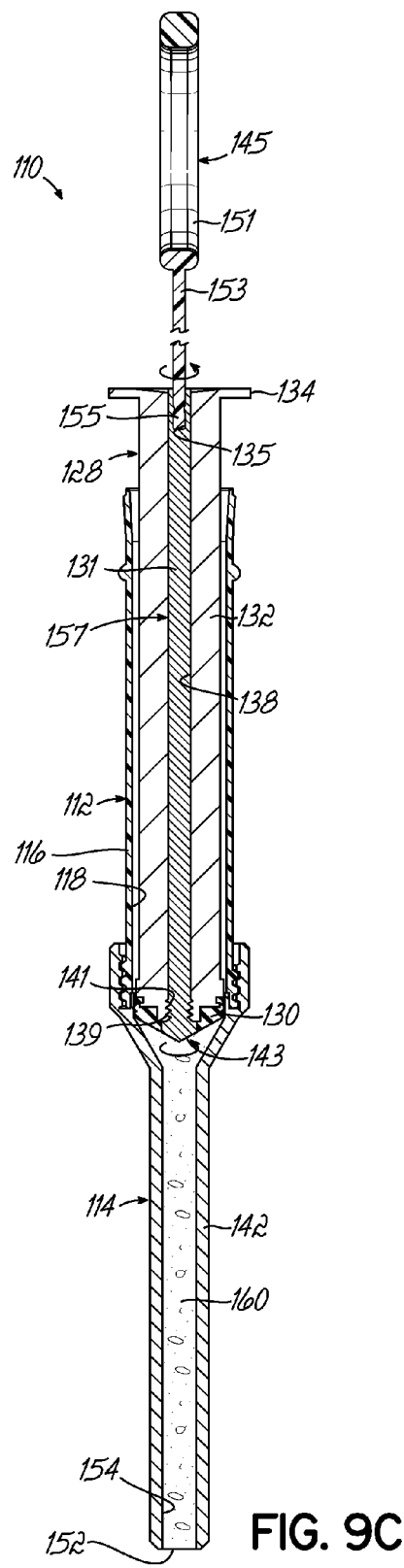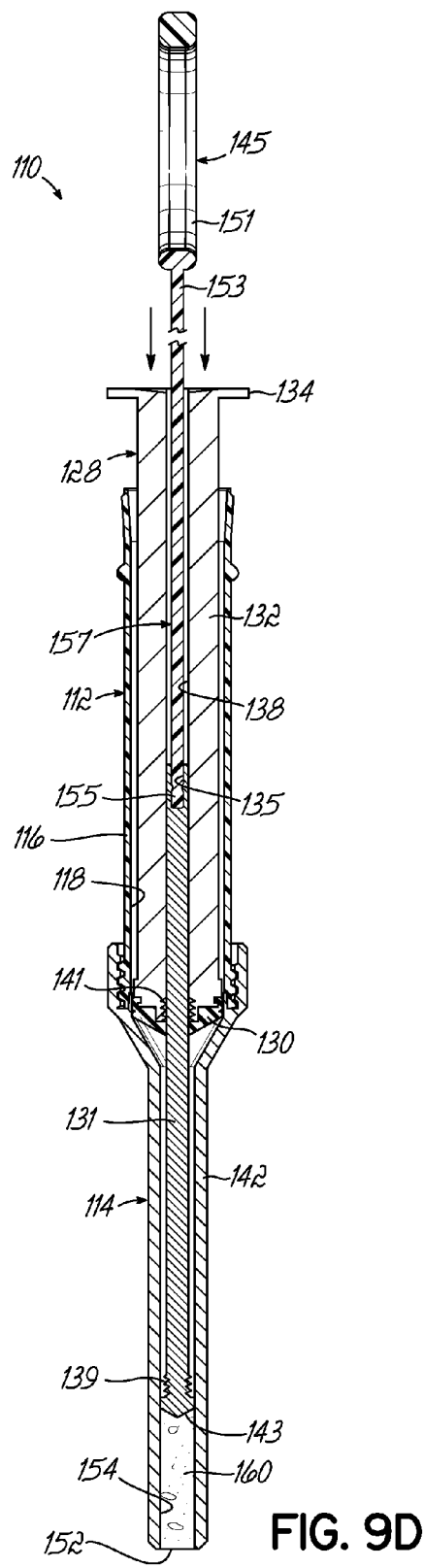

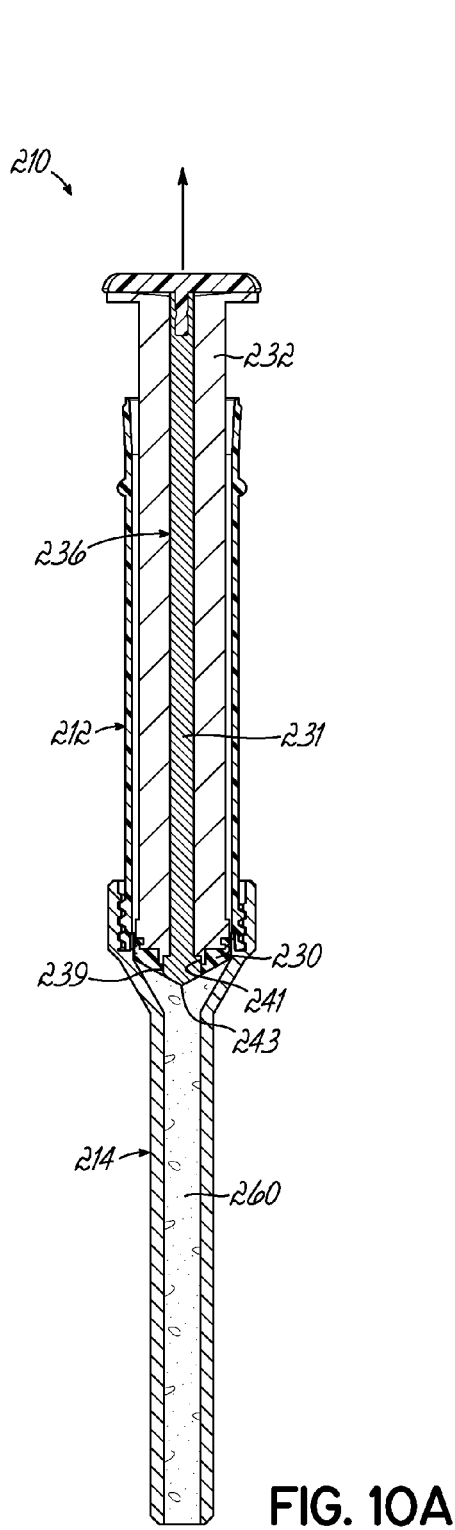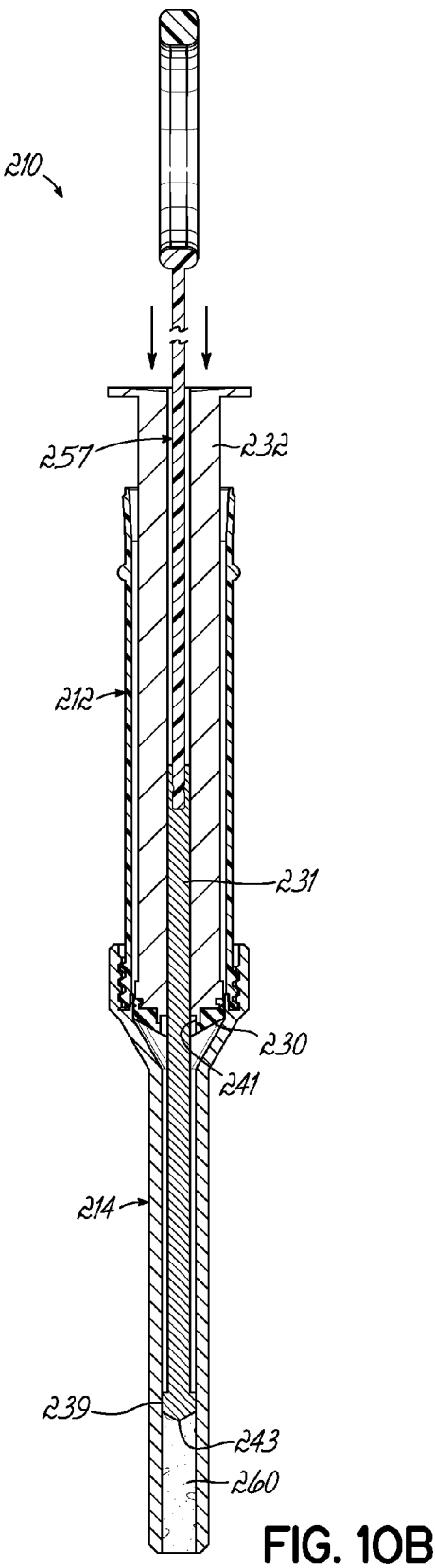
FIG. 10A
FIG. 10B

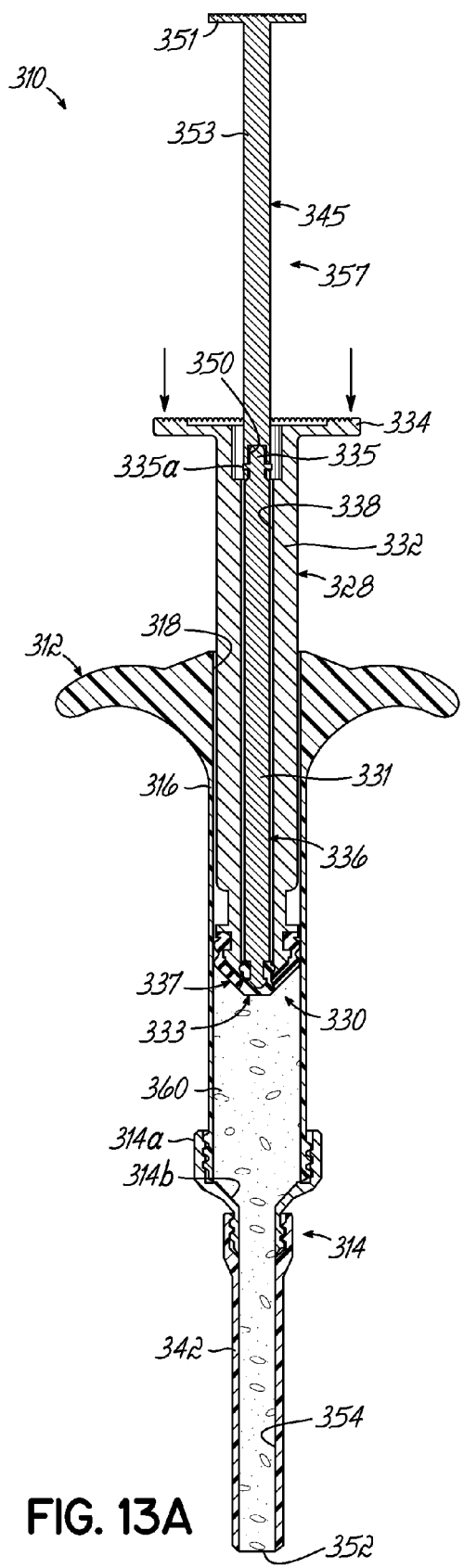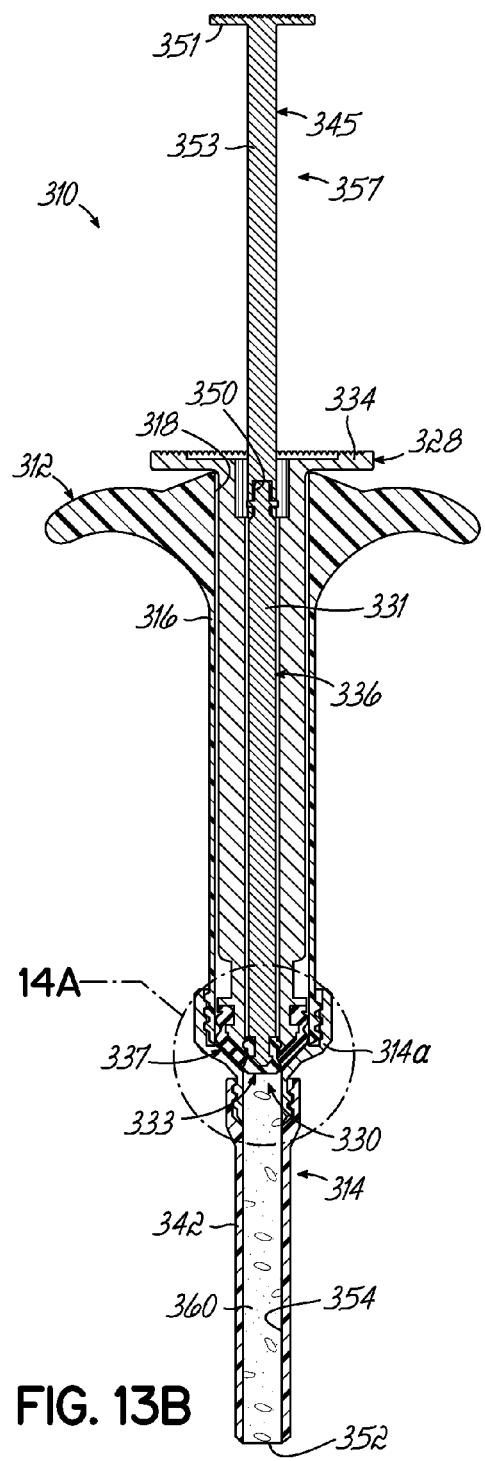
FIG. 13A
FIG. 13B

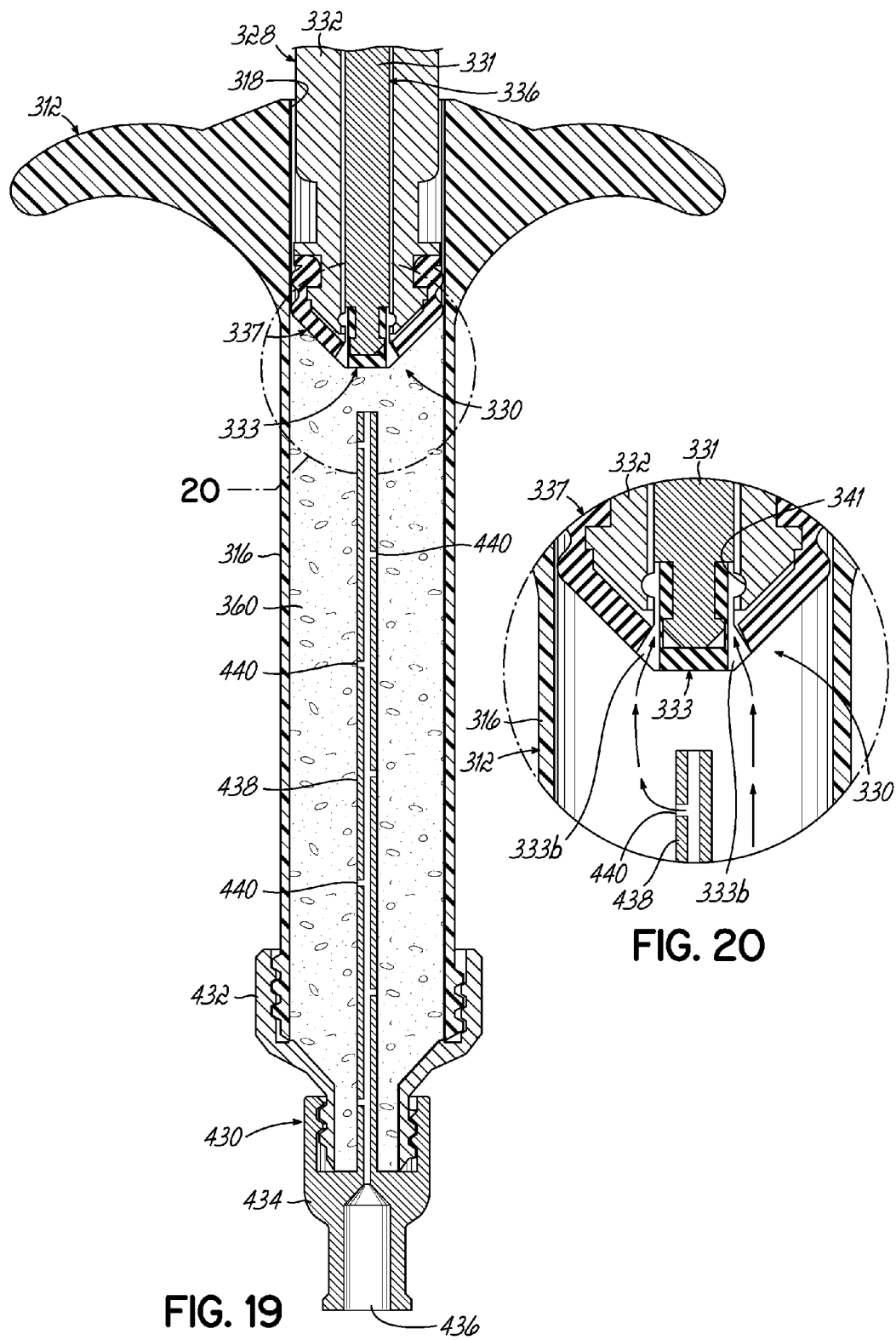

ASSEMBLY FOR DISPENSING BIOMATERIAL, PLUNGER THEREFOR, AND RELATED METHODS

CROSS-REFERENCE TO RELATED APPLICATION

This application claims the priority of Application Ser. No. 61/778,839 filed Mar. 13, 2013, the disclosure of which is hereby incorporated by reference herein.

FIELD OF THE INVENTION

The present invention generally relates to dispensing equipment, and more particularly to devices used for dispensing biomaterials such as bone graft materials.

BACKGROUND

Biomaterials are sometimes used in medical applications. For example, bone grafting is a surgical procedure for repairing bones and typically involves introducing a bone graft material (which is a type of biomaterial) into an area of bone that requires repair, such as a fracture. The bone graft material is intended to stimulate growth of healthy native bone tissue, and new native bone tissue may eventually replace the bone graft material completely. Bone graft material typically includes a combination of crushed bone and a liquid component, such as blood, plasma, or growth factors. Bone graft materials can be allograft (derived from a human other than the one receiving the graft), autograft (derived from the human receiving the graft), and synthetic (created from, for example, ceramics like calcium phosphates).

Bone graft materials are typically delivered to a surgical site using syringe-like delivery devices, which often include attachment devices, such as small diameter cannulus devices. In addition, the components of the bone graft material are sometimes brought together and combined to form the bone graft material in the delivery device. The bone graft material is dispensed from the delivery device. This often involves using a syringe plunger to advance an amount of bone graft material from a syringe and through an attachment device, and then dispensing the bone graft material from the attachment device at the surgical site. Once the syringe plunger is completely depressed in the syringe, all or nearly all of the bone graft material is expelled from the syringe. However, the attachment device still contains an amount of bone graft material, and further operation of the syringe plunger is ineffective for advancing that bone graft material out of the attachment device. This prevents the bone graft material that is trapped in the attachment device from being used during the surgical procedure, and leads to wasting an amount of the bone graft material. Wasting bone graft material is undesirable, however, as its components are costly. In addition, this drawback to current devices requires that more bone graft material be prepared than is actually required at the surgical site, in order to offset the amount that remains in the attachment device.

SUMMARY

According to one embodiment of the invention, an assembly is provided, and includes a dispensing syringe device and a cannulus device. The dispensing syringe device is configured to receive an amount of biomaterial and to dispense the biomaterial. The dispensing syringe device includes a syringe barrel for receiving the biomaterial, a discharge outlet for dispensing the biomaterial from the syringe barrel, and a plunger received in the syringe barrel. The plunger has a plunger body and a plunger passageway extending therethrough configured to receive a stylet. The cannulus device is configured to be coupled with the dispensing syringe device, to receive biomaterial from the dispensing syringe device, and to dispense the biomaterial. The cannulus device includes a cannulus passageway configured to receive the biomaterial and a dispensing opening configured for dispensing the biomaterial.

According to another embodiment of the invention, a method is provided for dispensing biomaterial. The method includes directing biomaterial from a dispensing syringe device into a passageway of a cannulus device using a plunger. The method further includes engaging biomaterial in the passageway of the cannulus device with a stylet, and directing biomaterial out of a dispensing opening of the cannulus device using the stylet.

According to yet another embodiment of the invention, a plunger is provided for use with a dispensing syringe device. The plunger includes a plunger body, a plunger head connected to the plunger body and sized to correspond with the shape of a syringe passageway of the dispensing syringe device, and a plunger passageway extending through the plunger body and the plunger head. The plunger passageway is configured to receive a stylet.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIGS. 5A-5B are cross-sectional views taken along line 5-5 of FIG. 4 and showing the stylet being inserted into the plunger passageway and then contacting the bone graft material and directing it through the cannulus device.

FIG. 6 is a partial cross-sectional view showing the dispensing tip of a cannulus device.

FIG. 9A-9D are cross-sectional and sequential operational views taken along line 9-9 of FIG. 8 and showing bone graft material being dispensed from the dispensing syringe device and the cannulus device, an extension portion being coupled with a shaft portion to form a stylet, and the stylet being used to contact the bone graft material in the cannulus device and direct it through the cannulus device.

FIGS. 10A and 10B are cross-sectional and sequential operational views generally like FIGS. 9B and 9D, and showing an assembly according to another embodiment of the invention.

FIGS. 13A and 13B are cross-sectional and sequential operational views showing bone graft material being dispensed from the dispensing syringe device and the cannulus device.

FIG. 19 is a cross-sectional view showing the hydration device coupled with the syringe barrel such that a tubular member of the hydration device is surrounded by bone graft material in the syringe barrel.

FIG. 20 is an enlarged view showing the circled region of FIG. 19, and showing a fluid component moving from the tubular member into the bone graft material, and air in the bone graft material escaping through vents in a stopper element of a plunger plug.

DETAILED DESCRIPTION

Figure 1:
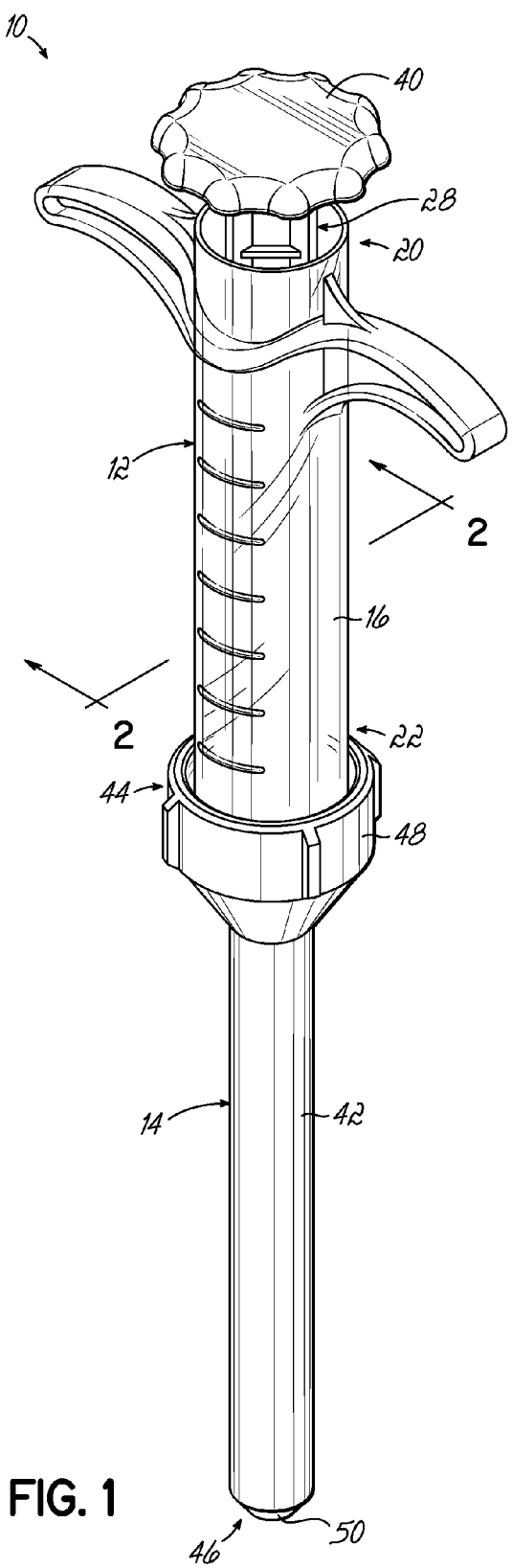
FIG. 1 is a perspective view showing an assembly constructed according to the concepts of the present invention and including a dispensing syringe device and a cannulus device.

Referring to the figures, and beginning with FIG. 1, an exemplary assembly 10 is shown and includes a dispensing syringe device 12 and a cannulus device 14. As will become apparent from the following description, the assembly 10 is used to dispense biomaterial, such as to a surgical site. For example, in the embodiments shown and described, the biomaterial that is dispensed is a bone graft material, such as what is used in a bone grafting procedure. The dispensing syringe device 12 provides bone graft material to the reduced diameter cannulus device 14, and the bone graft material is dispensed from the cannulus device 14 to the surgical site.

Figure 2:
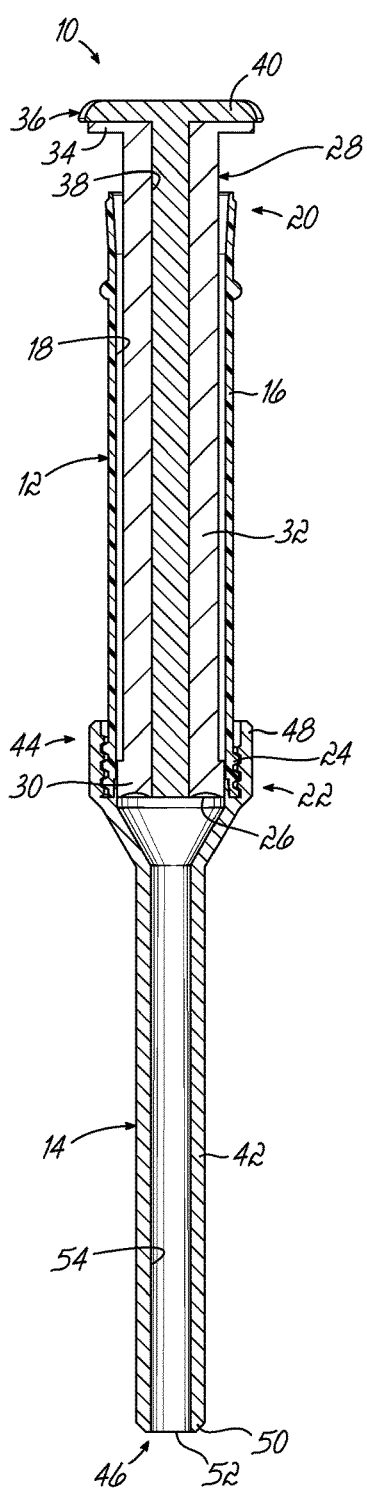
FIG. 2 is a cross-sectional view taken along line 2-2 of FIG. 1.

Referring first to FIGS. 1 and 2, the dispensing syringe device 12 includes a syringe barrel 16 that has within it a syringe passageway 18. The syringe barrel 16 extends between a first end 20 and a second end 22. The syringe barrel 16 includes a threaded locking tip 24 generally near the second end 22. The threaded locking tip 24 is configured to be coupled with the cannulus device 14, as will be described below. A discharge outlet 26 is defined in the syringe barrel 16 near the second end 22.

The dispensing syringe device 12 also includes a plunger 28 that is received and moves in the syringe passageway 18. The plunger 28 generally includes a plunger head 30 that is sized to correspond with the shape of the syringe passageway 18. The plunger head 30 is configured for pushing bone graft material out of the syringe passageway 18. A plunger body 32 is connected with the plunger head 30 and extends along the lengthwise direction of the syringe passageway 18. The plunger body 32 is also connected with a plunger base 34 opposite the plunger head 30.

As shown in FIG. 2, the plunger 28 also includes a plunger plug 36 that is received in a plunger passageway 38. The plunger passageway 38 is generally centrally disposed in the plunger 28 and extends along the lengthwise direction of the plunger 28 between the plunger head 30 and the plunger base 34. In particular, the plunger passageway 38 extends through the plunger head 30, the plunger body 32, and the plunger base 34. In the embodiment shown, the plunger plug 36 extends in the plunger passageway 38 from the plunger head 30 to the plunger base 34. The plunger plug 36 includes a plug flange 40 that rests on the plunger base 34 when the plunger plug 36 is installed in the plunger 28.

As shown, the plunger head 30 has a generally cylindrical shape, and is defined partly by the plunger body 32 and partly by the plunger plug 36 when the plunger plug 36 is installed in the plunger 28. However, other shapes and configurations are also possible, such as a generally frusto-conically shaped plunger head, for example.

The cannulus device 14 is removably coupled to the dispensing syringe device 12 at the second end 22 thereof. The cannulus device 14 has a generally tubular body 42 and extends between a first end 44 and a second end 46. The body 42 includes a threaded attachment cap 48 near the first end 44 and a dispensing tip 50 near the second end 46, which includes a dispensing opening 52. A cannulus passageway 54 extends through the body 42 and communicates with the dispensing tip 50. The cannulus passageway 54 has a generally reduced diameter as compared with the syringe passageway 18.

The threaded attachment cap 48 is configured for connecting with the threaded locking tip 24 of the syringe barrel 16 so as to create a removable connection between the dispensing syringe device 12 and the cannulus device 14, as shown in the figures. In particular, the cannulus device 14 may be removed from the dispensing syringe device 12 in order to place an amount of bone graft material into the syringe barrel 16 for a dispensing operation. The cannulus device 14 may be reattached to the dispensing syringe device 12 for dispensing the bone graft material.

Figure 3A:
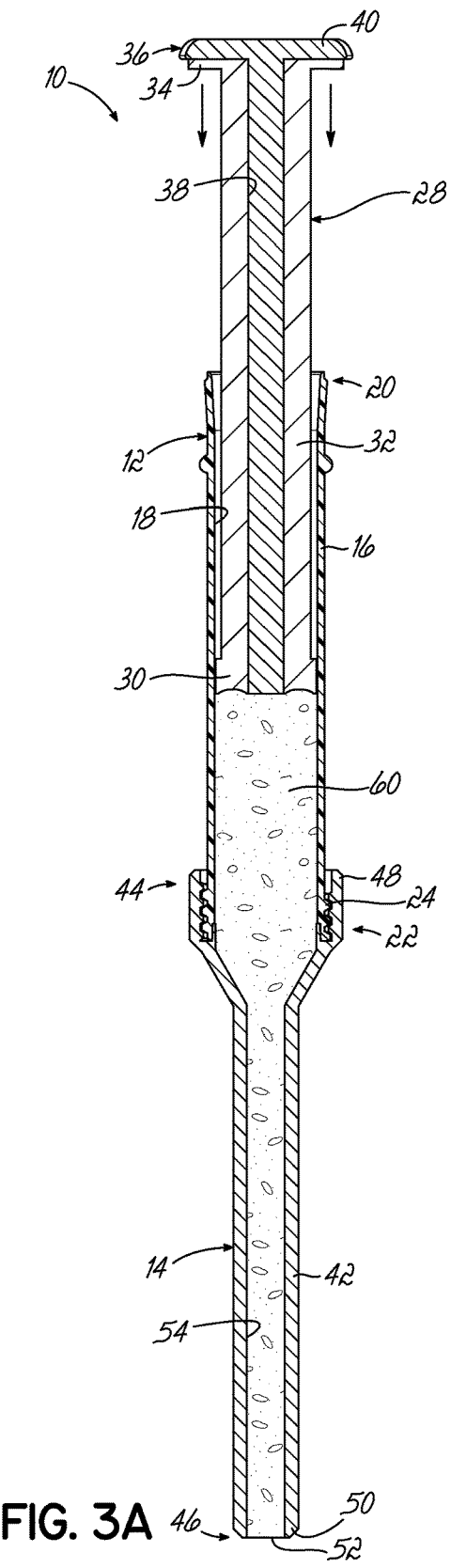
FIGS. 3A-3C are cross-sectional views like FIG. 2, and showing bone graft material being dispensed from the dispensing syringe device and the cannulus device, and then a plunger plug being removed from the plunger of the dispensing syringe device.
Figure 3B:
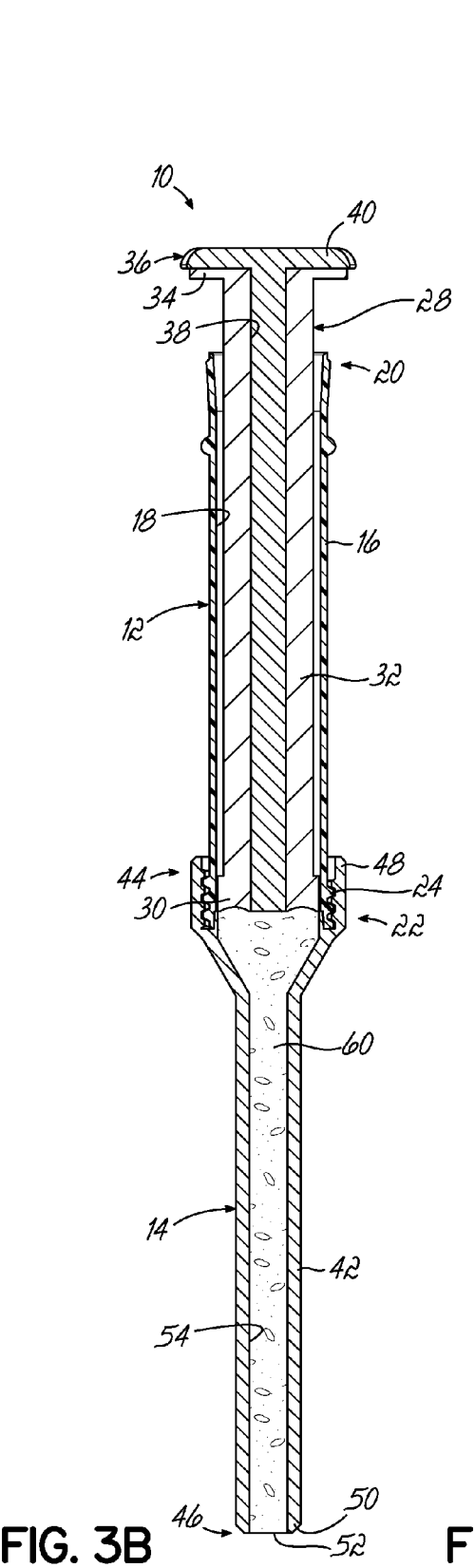
Figure 3C:
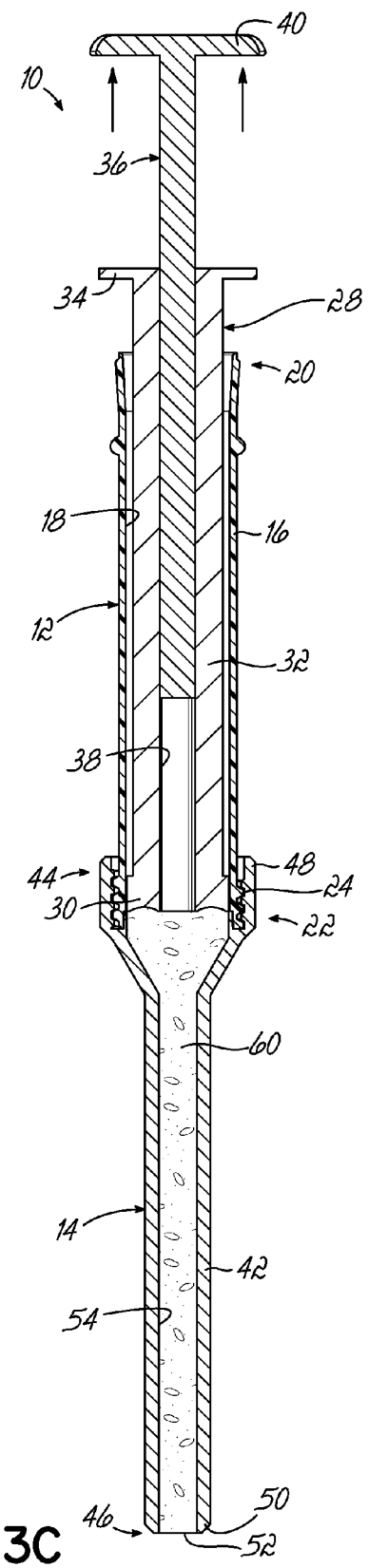

Referring next to FIGS. 3A-3C, the assembly 10 is used for dispensing bone graft material 60 that has been introduced into the dispensing syringe device 12. In particular, downward movement of the plunger 28 directs the bone graft material 60 contained in the syringe passageway 18 out of the syringe barrel 16 and into the cannulus passageway 54 of the cannulus device 14. Further downward movement of the plunger 28 directs the bone graft material through the cannulus passageway 54, and out the dispensing opening 52.

However, movement of the plunger 28 is confined to the syringe barrel 16, and so the plunger 28 is not effective for dispensing all of the bone graft material 60 from the assembly 10. Particularly, the plunger 28 cannot dispense all of the bone graft material 60 in the cannulus device 14, as shown in FIG. 3B. After the plunger 28 has been pushed as far as possible in the syringe barrel 16, all or nearly all of the bone graft material 60 has been dispensed from the syringe barrel 16, as shown in FIG. 3B. However, an amount of the bone graft material 60 remains in the cannulus device 14, as also shown in FIG. 3B.

To direct the bone graft material 60 out of the cannulus device 14, a stylet 70 is used to engage and push the bone graft material 60 out of the cannulus device 14. In particular, the stylet 70 is inserted through the plunger passageway 38 and advanced toward the bone graft material 60 in the cannulus device 14.

Figure 4:
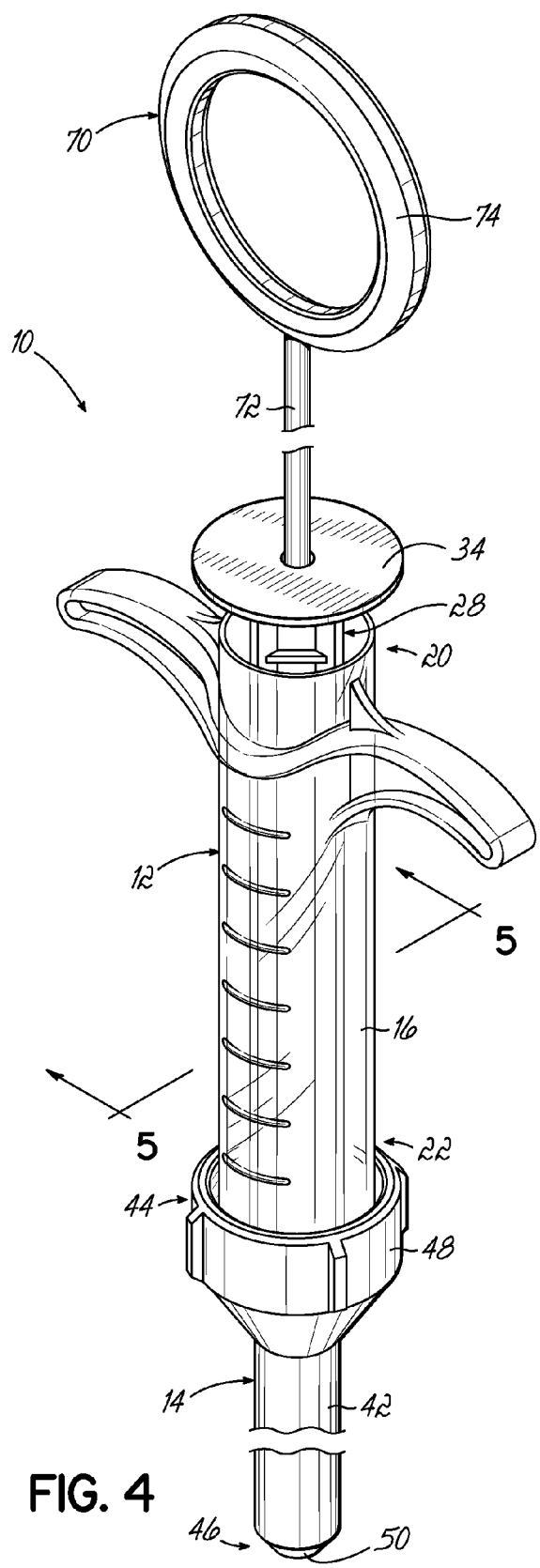
FIG. 4 is a perspective view of an assembly like in FIG. 1 and showing a stylet inserted into the plunger passageway of the plunger of the dispensing syringe device.

To make room for the stylet 70, the plunger plug 36 is removed from the plunger 28, as shown in FIG. 3C. In particular, the plunger plug 36 is removed from the plunger passageway 38. For example, a user can grasp the plug flange 40 and move the plunger plug 36 away from the plunger 28. Then, as shown in FIGS. 4 and 5A-5B, the stylet 70 is inserted into and through the plunger passageway 38, and is used to direct the bone graft material 60 out of the cannulus device 14.

The stylet 70 includes a main body portion or shaft 72 that is attached to a handle 74. The shaft 72 is configured to fit and slidably move within the plunger passageway 38 of the plunger 28 and the cannulus passageway 54 of the cannulus device 14. The shaft 72 includes a head portion or tip 76 that is generally opposite from the handle 74 and is generally sized to correspond with the internal shape of the cannulus passageway 54. The tip 76 is configured for pushing bone graft material 60 out of the cannulus passageway 54. The handle 74 provides a location for a user to grasp the stylet 70 and is generally ring-shaped, although other handle shapes are also possible. The stylet 70 is configured to engage the bone graft material 60 that is in the cannulus passageway 54 and advance it toward and out of the dispensing opening 52.

While the cannulus passageway 54 shown in FIGS. 3A-3C and 5A-5B has a generally straight profile near the dispensing opening 52, an alternative configuration is shown in FIG. 6. FIG. 6 shows the cannulus passageway 54 is defined by a taper region 80 which tapers radially inwardly near the dispensing opening 52. The taper region 80 forms a stop for engaging with the tip 76 of the stylet 70, as shown, and for preventing the tip 76 from reaching or exiting the dispensing opening 52.

Referring next to FIGS. 7-9D, an assembly 110 is shown that generally includes a dispensing syringe device 112 and a cannulus device 114. The assembly 110 is generally similar to the assembly 110, except as further described below.

The dispensing syringe device 112 includes a syringe barrel 116 that has within it a syringe passageway 118. The dispensing syringe device 112 includes a plunger 128 that is received and moves in the syringe passageway 118. The plunger 128 generally includes a plunger head 130 that is sized to correspond with the shape of, and push bone graft material out of, the syringe passageway 118. A plunger body 132 is connected with the plunger head 130 and is also connected with a plunger base 134 opposite the plunger head 130. The plunger 128 also includes a generally centrally disposed plunger passageway 138 that extends through the plunger head 130, the plunger body 132, and the plunger base 134.

Figure 7:
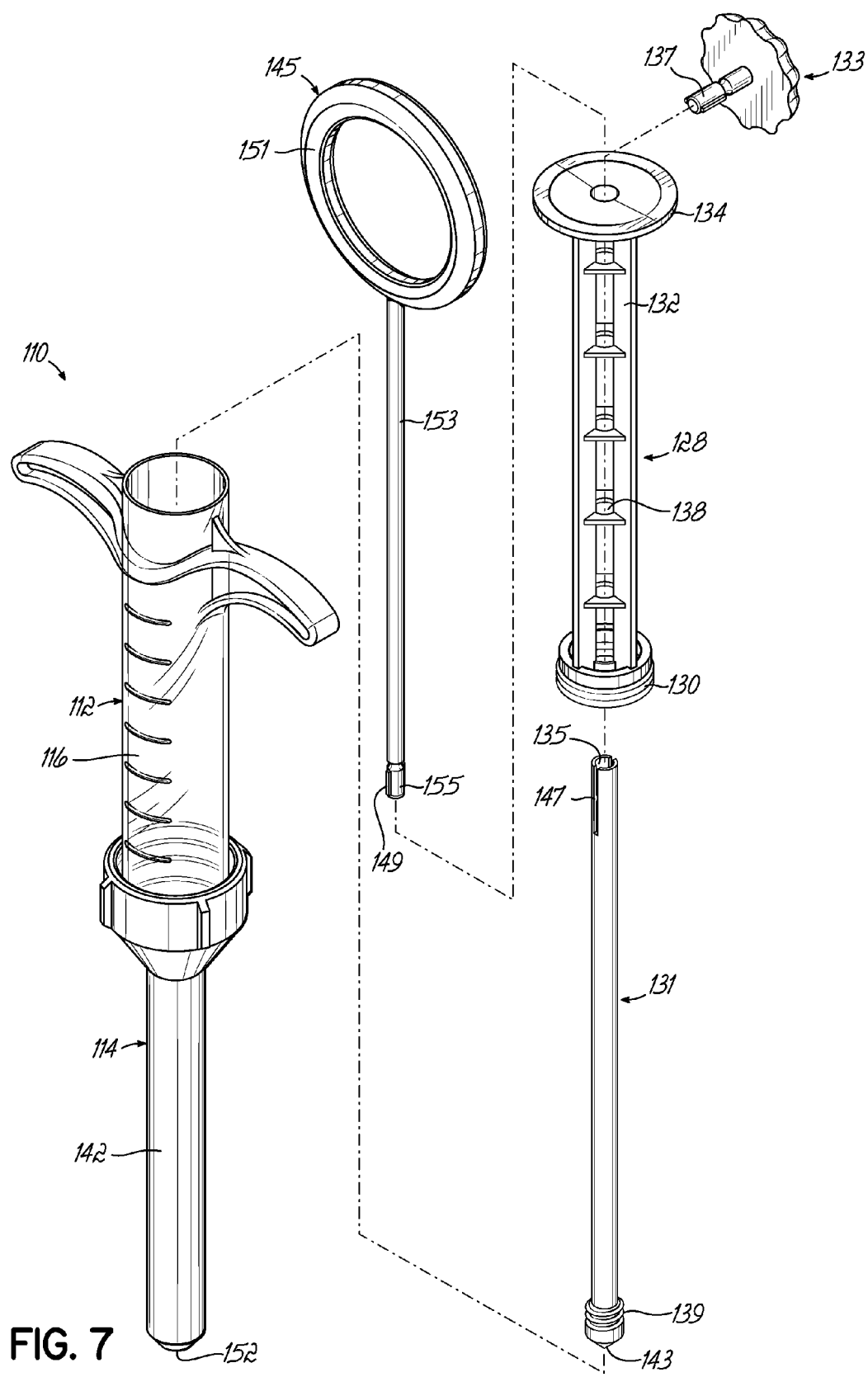
FIG. 7 is a disassembled perspective view showing components of an assembly according to another embodiment of the invention, and including a dispensing syringe device and a cannulus device.
Figure 8:
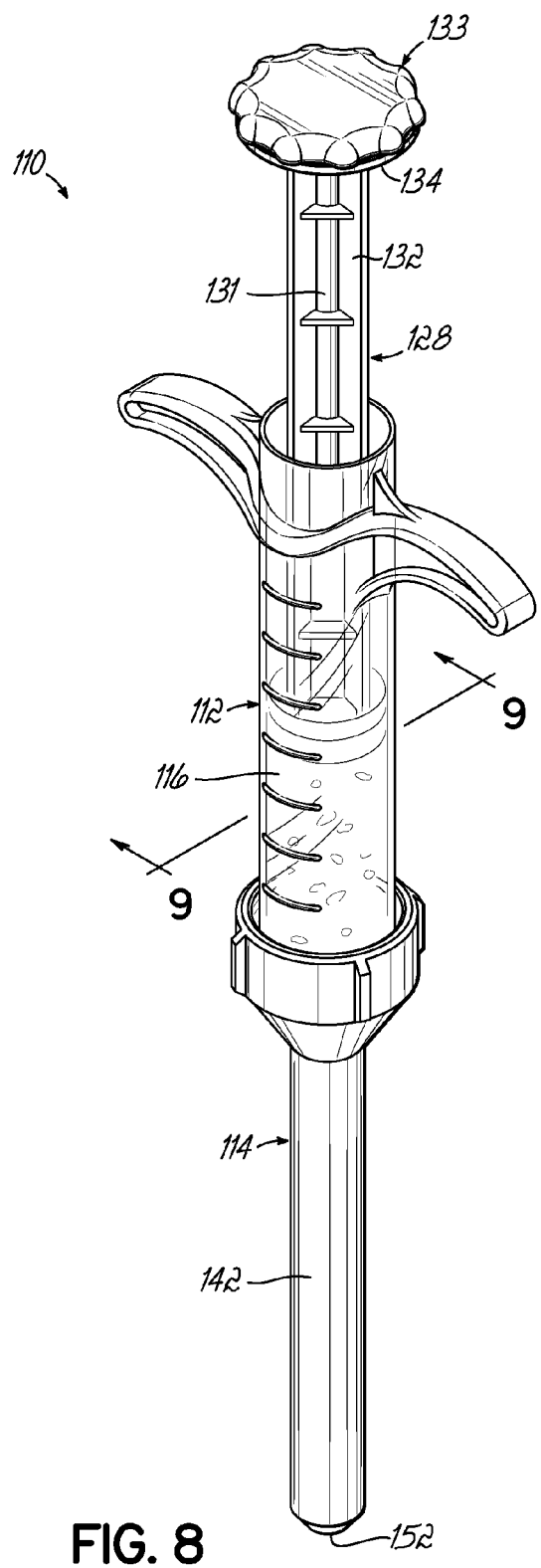
FIG. 8 is an assembled perspective view showing the assembly of FIG. 7.
Figure 11:
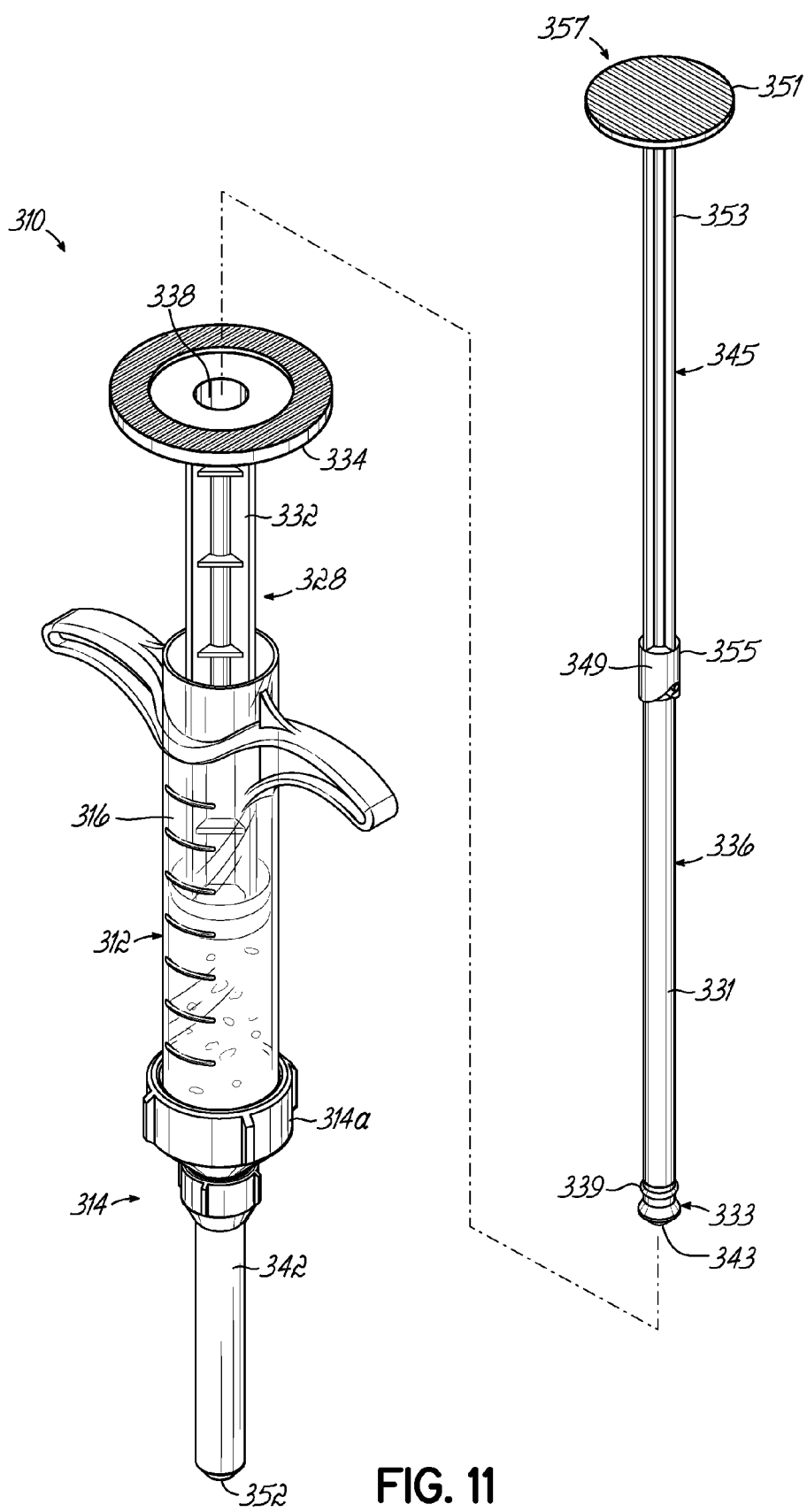
FIG. 11 is a disassembled perspective view showing components of an assembly according to another embodiment of the invention, and including a dispensing syringe device and a cannulus device.

A plunger plug 136 is generally situated in the plunger passageway 138, and includes a shaft portion 131 and a cap portion 133 (FIGS. 7 and 9A). The cap portion 133 is configured to be removably coupled with the shaft portion 131 (FIG. 9C). The shaft portion 131 includes a socket 135 that is configured to receive a stem 137 of the cap portion 133. In addition, the cap portion 133 includes a flange 140 that rests on the plunger base 134 when the cap portion 133 is installed in the plunger 128, as shown in FIGS. 9A and 9B.

The plunger plug 136 includes structure for forming a threaded relationship with the plunger body 132. In particular, the shaft portion 131 includes a threaded portion 139 that is configured to be engaged with a threaded portion 141 of the plunger body 132, as shown in FIGS. 9A-9C. For example, in the embodiment shown, the threaded portion 139 of the shaft portion 131 is situated near a tip 143 of the shaft portion 131, and the threaded portion 141 of the plunger body 132 is situated near the region of the plunger head 130. When the threaded portions 139, 141 are engaged (FIGS. 9A-9C), the shaft portion 131 is prevented from moving in the lengthwise direction with respect to the plunger body 132. As shown, the plunger body 132 and the plunger plug 136 define a generally frusto-conically shaped plunger head 130 when the plunger plug 136 is installed in the plunger 128, but other shapes and configurations are also possible, such as the generally cylindrical shape described above.

The shaft portion 131 is configured to be rotated with respect to the plunger body 132, such as to rotate the threaded portions 139, 141 into and out of engagement with one another. To that end, the shaft portion 131 includes structure for mating with an extension device 145, such that rotation of the extension device 145 causes rotation of the shaft portion 131. As best seen in FIG. 7, the socket 135 of the shaft portion 131 includes lengthwise extending slots 147. The slots 147 are configured to receive and be engaged by nubs 149 on the extension device 145.

The extension device 145 is configured to be removably coupled with the shaft portion 131. The extension device 145 generally includes a handle 151 connected with a shaft 153 which terminates in a tip 155. In the embodiment shown, the nubs 149 extend radially outward from the shaft 153 near the tip 155. The shaft 153 is sized to fit and slidably move within the plunger passageway 138 of the plunger body 132.

The extension device 145 is coupled with the shaft portion 131 by inserting the tip 155 of the extension device 145 into the socket 135 of the shaft portion 131, as shown in FIG. 9C. In particular, the nubs 149 are aligned with the slots 147, and the tip 155 is pushed into the socket 135. When the nubs 149 are thus positioned in the slots 147, rotation of the extension device 145 will cause rotation of the shaft portion 131, as indicated in FIG. 9C. In addition, downward movement of the extension device 145 will cause downward movement of the shaft portion 131.

The cannulus device 114 is removably coupled to the dispensing syringe device 112. The cannulus device has a generally tubular body 142 having a dispensing opening 152. A cannulus passageway 154 extends through the body 142. The shaft portion 131 of the plunger plug 136, including the tip 143, is sized to fit and slidably move within the cannulus passageway 154. In particular, the tip 143 is configured to push bone graft material 160 out of the cannulus passageway 154.

The assembly 110 is used for dispensing bone graft material 160 that has been introduced into the dispensing syringe device 112. In particular, downward movement of the plunger 128 directs the bone graft material 160 contained in the syringe passageway 118 out of the syringe barrel 116 and into the cannulus passageway 154 of the cannulus device 114. Further downward movement of the plunger 128 directs the bone graft material 160 through the cannulus passageway 154, and out the dispensing opening 152. During these steps, the shaft portion 131 is engaged with respect to the plunger body 132, and generally does not move with respect thereto. In particular, the threaded portion 139 of the shaft portion 131 is engaged with the threaded portion 141 of the plunger body 132, as shown in FIGS. 9A and 9B.

Movement of the plunger 128 is confined to the syringe barrel 116, and so the plunger 128 cannot dispense all of the bone graft material 160 from the assembly 110. In a similar manner as described above, the plunger 128 cannot dispense all of the bone graft material 160 in the cannulus device 114. After the plunger 128 has been pushed as far as possible in the syringe barrel 116, all or nearly all of the bone graft material 160 has been dispensed from the syringe barrel 116, but an amount of the bone graft material 160 is still present in the cannulus device 114, as shown in FIG. 9B. The shaft portion 131 and the extension device 145, which together form a stylet 157, are used to engage and push the bone graft material 160 out of the cannulus device.

In particular, the cap portion 133 is removed from the shaft portion 131 by removing them stem 137 of the cap portion 133 from the socket 135 of the shaft portion 131, as indicated in FIG. 9B. Then, the extension device 145 is coupled with the shaft portion 131, as shown in FIG. 9C, to form the stylet 157. The stylet 157 is then rotated in order to disengage the threaded portions 139, 141 from each other. In particular, the extension device 145 is rotated so that the shaft portion 131 is rotated to cause the threaded portion 139 to be advanced away from the threaded portion 141 of the plunger body 132 and toward the dispensing opening 152 of the cannulus device 114.

As shown in FIG. 9D, once the threaded portions 139, 141 are disengaged from each other, the stylet 157 can be used to direct the bone graft material 160 out of the cannulus device 114. In particular, the tip 143 of the shaft portion 131 engages the bone graft material 160 that is in the cannulus passageway 154 and advances the bone graft material 160 toward and out of the dispensing opening 152.

Referring next to FIGS. 10A and 10B, an assembly 210 is shown that generally includes a dispensing syringe device 212 and a cannulus device 214. The assembly 210 is generally similar to the assemblies 10 and 110, except as further described below.

The cannulus device 214 is substantially similar to the cannulus device 114 described in association with FIGS. 7-9D. The dispensing syringe device 212 is substantially similar to the dispensing syringe device 112 described in association with FIGS. 7-9D, except with respect to the construction of the plunger body and the plunger plug. In FIGS. 10A and 10B, a plunger body 232 and a plunger plug 236 do not include threaded portions like the threaded portions 141, 139 on the plunger body 132 and plunger plug 136. Rather, the plunger body 232 and the plunger plug 236 have a generally smooth interface in the region of the plunger head 230. In particular, a shaft portion 231 of the plunger plug 236 includes a smooth-walled portion 239 generally near a tip 243 of the shaft portion 231. A plunger body 232 includes a smooth-walled portion 241 near a plunger head 230. The respective smooth-walled portions 239, 241 allow the shaft portion 231 to be easily moved away from the plunger body 232.

The assembly 210 can be used to dispense bone graft material 260 in a manner substantially similar to what is described above for assembly 110, except that it is not necessary to rotate the plunger plug 236 to disengage it from the plunger body 232. In particular, the shaft portion 231 of the plunger plug 236 can be combined with an extension device to form a stylet 257 that is used to advance the bone graft material 260 out of the cannulus device 214.

Referring next to FIGS. 11-14C, an assembly 310 is shown that generally includes a dispensing syringe device 312 and a cannulus device 314. The assembly 310 is generally similar to the assemblies 10, 110, and 210, except as further described below.

The dispensing syringe device 312 includes a syringe barrel 316 that has within it a syringe passageway 318. The dispensing syringe device 312 includes a plunger 328 that is received and moves in the syringe passageway 318. The plunger 328 generally includes a plunger head 330 that is sized to correspond with the shape of, and push bone graft material out of, the syringe passageway 318. A plunger body 332 is connected with the plunger head 330 and is also connected with a plunger base 334 opposite the plunger head 330. The plunger 328 also includes a generally centrally disposed plunger passageway 338 that extends through the plunger head 330, the plunger body 332, and the plunger base 334.

A plunger plug 336 is generally situated in the plunger passageway 338, and includes a shaft portion 331 and a stopper element 333, which in the embodiment shown is configured to be removably coupled with the shaft portion 331. In particular, the shaft portion 331 includes a first post 331a having a flared portion 331b, and the stopper element 333 includes a socket 333a. When the stopper element 333 is coupled with the shaft portion 331, the flared portion 331b and the first post 331a of the shaft portion 331 are received in the socket 333a of the stopper element 333. The stopper element 333 generally defines a tip 343 of the shaft portion 331 or the plunger plug 336, and may be formed of an elastomeric material, for example.

The plunger plug 336 includes structure for forming a snap-fit relationship with the plunger body 332. In particular, the stopper element 333 of the plunger plug 336 includes a rib 339 that extends from an exterior of the stopper element 333. In the embodiment shown, the rib 339 extends around the entire circumference of the stopper element 333. Other configurations are also possible, wherein the rib 339 includes one or more segments that do not extend around the entire circumference. The plunger body 332 includes a groove 341 for receiving the rib 339. In particular, the groove 341 extends radially outward from the plunger passageway 338 in the region of the plunger head 330. In the embodiment shown, the groove 341 is annular and extends entirely around the plunger passageway 338 in order to receive the circumferential groove 341. The plunger plug 336 "snaps" into engagement with the plunger body 332 when the rib 339 is received in the groove 341. The plunger plug 336 can be pushed out of engagement with the plunger body 332 by applying sufficient force to move the rib 339 out of the groove 341. When the rib 339 is engaged with the groove 341, the plunger plug 336 is prevented from moving in the lengthwise direction with respect to the plunger body 332.

The plunger head 330 is partly formed by a plunger head stopper element 337. In the embodiment shown, the plunger head stopper element 337 is configured to be removably coupled with the plunger body 332. In particular, the plunger body 332 includes a first attachment flange 328a and a second attachment flange 328b. The plunger head stopper element 337 includes a socket 337a and an attachment band 337b. When the plunger head stopper element 337 is coupled with the plunger body 332, the first attachment flange 328a is received in the socket 337a, and the attachment band 337b generally surrounds the plunger body 332 between the first attachment flange 328a and the second attachment flange 328b. The plunger passageway 338 extends through the plunger head stopper element 337. The plunger head stopper element 337 includes an inclined wall 337c, which extends at an angle of approximately 45° with respect to the plunger passageway 338. The plunger head stopper element 337 may be formed of an elastomeric material, for example.

The plunger head 330 is also partly formed by the plunger plug 336 when the plunger plug 336 is installed in the plunger 328. Together the plunger head stopper element 337 and the plunger plug 336 define a generally frusto-conically shaped plunger head 330, but other shapes and configurations are also possible, such as the generally cylindrical shape described above.

The shaft portion 331 includes structure for mating with an extension device 345. In particular, the shaft portion 331 includes a second post 335 having transversely extending nubs 335a. The second post 335 is positioned on the shaft portion 331 generally opposite from the first post 331a. The extension device 345 is configured to be removably coupled with the shaft portion 331, and includes a finger ledge 351 connected with a shaft 353 which terminates in a tip 355. The finger ledge 351 provides a surface where a user can press on the extension device 345. For example, a user can use one or more of his fingers, such as his thumb, to press on the finger ledge 351 and move the extension device 345. The shaft 353 and the tip 355 are sized to fit and slidably move within the plunger passageway 338.

The tip 355 includes a generally tubular collar 349 that defines within it a socket 350. The socket 350 is configured to receive the second post 335 of the shaft portion 331. The collar 349 also includes channels 356 that are configured to engage and receive the nubs 335a on the second post 335. As shown, the channels 356 extend radially outward from the socket 350, and follow a curved path upwardly from a leading edge of the tip 355.

The extension device 345 is coupled with the shaft portion 331 by directing the collar 349 over the second post 335 so that the second post 335 is received in the socket 350. The extension device 345 is rotated so the channels 356 of the collar 349 engage and receive the nubs 335a. Once the extension device 345 is coupled with the shaft portion 331, downward movement of the extension device 345 will cause downward movement of the shaft portion 331.

Figure 14A:
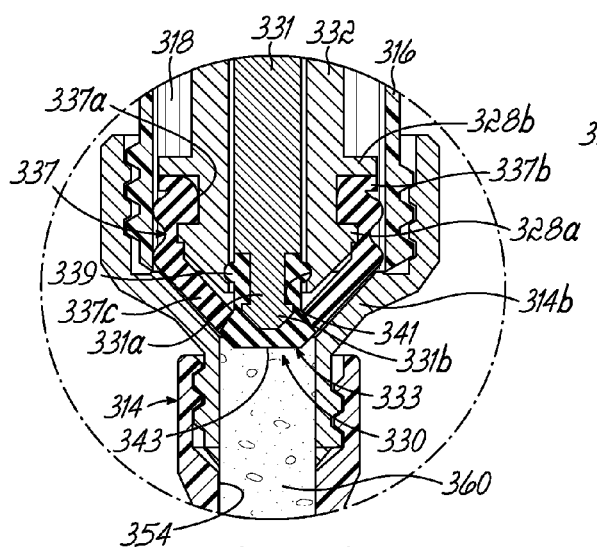
FIG. 14A is an enlarged view showing the circled region of FIG. 13B, and showing a rib on a plunger plug engaged with a groove on a plunger body.

The cannulus device 314 is removably coupled to the dispensing syringe device 312. In particular, the cannulus device 314 includes an attachment portion 314a that is configured to be coupled with the syringe barrel 316 of the dispensing syringe device 312, such as by using complementary threaded portions on the attachment portion 314a and the syringe barrel 316. The attachment portion 314a includes a tapered or sloped wall portion 314b. The sloped wall portion 314b is inclined at an angle, such as to be generally complementary to the inclined wall 337c of the plunger head stopper element 337, as shown in FIG. 14A. By using these complementary shapes between the plunger 328 (the inclined wall 337c of the plunger head stopper element 337) and the cannulus device 314 (the sloped wall portion 314b of the attachment portion 314a), the amount of bone graft material that is left in the syringe barrel 316 can be minimized.

The cannulus device 314 also has a generally tubular body portion 342 having a dispensing opening 352. The body portion 342 is configured to be coupled with the attachment portion 314a, such as by using complementary threaded portions on the respective portions 342, 314a, for example. A cannulus passageway 354 extends through the body portion 342. The shaft portion 331 of the plunger plug 336, including the tip 343, is sized to fit and slidably move within the cannulus passageway 354. In particular, the tip 343 is configured to push bone graft material 360 out of the cannulus passageway 354.

The assembly 310 is used for dispensing bone graft material 360 that has been introduced into the dispensing syringe device 312. In particular, downward movement of the plunger 328 directs the bone graft material 360 contained in the syringe passageway 318 out of the syringe barrel 316 and into the cannulus passageway 354 of the cannulus device 314. Further downward movement of the plunger 328 directs the bone graft material 360 through the cannulus passageway 354, and out the dispensing opening 352. During these steps, the shaft portion 331 is engaged with respect to the plunger body 332, and generally does not move with respect thereto. In particular, the rib 339 is received in the groove 341, as shown in FIG. 14A.

Movement of the plunger 328 is confined to the syringe barrel 316, and so the plunger 328 cannot dispense all of the bone graft material 360 from the assembly 310. In a similar manner as described above, the plunger 328 cannot dispense all of the bone graft material 360 in the cannulus device 314. After the plunger 328 has been pushed as far as possible in the syringe barrel 316, all or nearly all of the bone graft material 360 has been dispensed from the syringe barrel 316, but an amount of the bone graft material 360 is still present in the cannulus device 314, as shown in FIG. 13B. The shaft portion 331 and the extension device 345, which together form a stylet 357, are used to engage and push the bone graft material 360 out of the cannulus device. The stylet 357 also includes the stopper element 333, which forms the tip 343 of the shaft portion 331.

In particular, the extension device 345 is coupled with the shaft portion 331, as shown in FIG. 13A, to form the stylet 357. The stylet 357 is pushed downwardly in order to disengage the rib 339 from the groove 341. In particular, the extension device 345 is pushed so that the shaft portion 331 is moved downwardly to cause the tip 343 to be moved toward the dispensing opening 352.

Figure 14B:
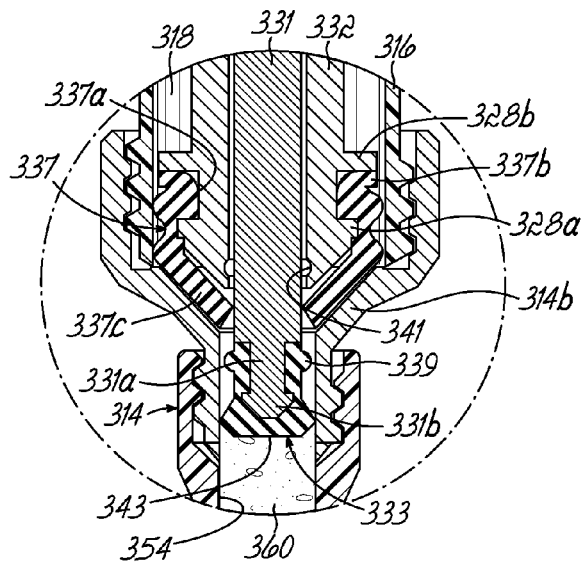
FIG. 14B is an enlarged view like FIG. 14A, but showing the rib out of engagement with the groove.
Figure 14C:
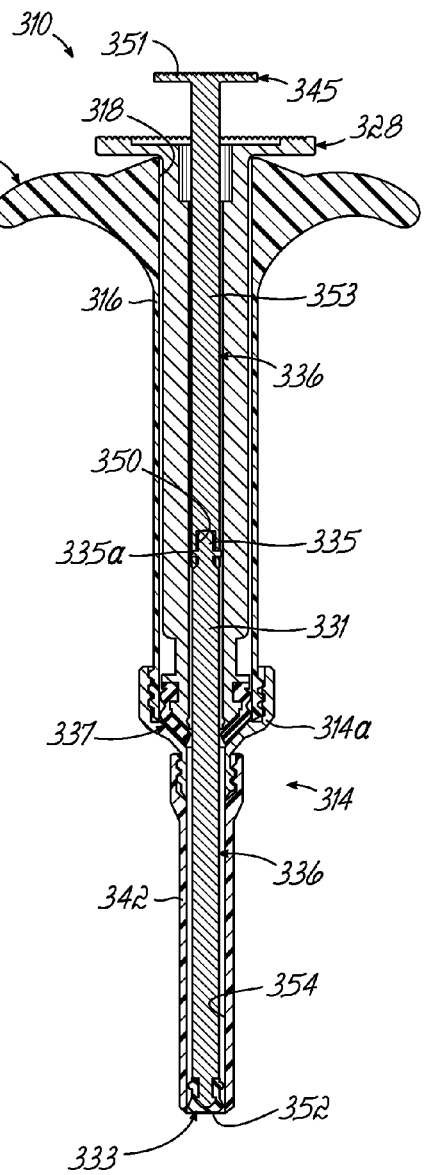
FIG. 14C is a cross-sectional view showing bone graft material being further dispensed from the dispensing syringe device and the cannulus device after the rib is disengaged from the groove.

As shown in FIGS. 14B and 14C, once the rib 339 and the groove 341 are disengaged from each other, the stylet 357 can be used to direct the bone graft material 360 out of the cannulus device. In particular, the stylet 357 is moved downwardly and the tip 343 engages the bone graft material 360 that is in the cannulus passageway 354 and advances the bone graft material 360 toward and out of the dispensing opening 352.

Referring next to FIGS. 15-17C, components of the assembly 310 are shown, except with an alternative cannulus device 400 and an alternative extension device 402. In particular, the cannulus device 400 has a much longer tubular body portion 404 (FIG. 15) than the tubular body portion 342 shown in FIGS. 11-14C.

Cannulus devices of different lengths may be used in different applications, for example. In situations where a long cannulus device is used, a generally correspondingly long stylet is required in order to direct bone graft material out of the entire length of the cannulus device. If a stylet is not sufficiently long, it will not be able to direct most or all of the bone graft material out of the cannulus device.

Figure 12:
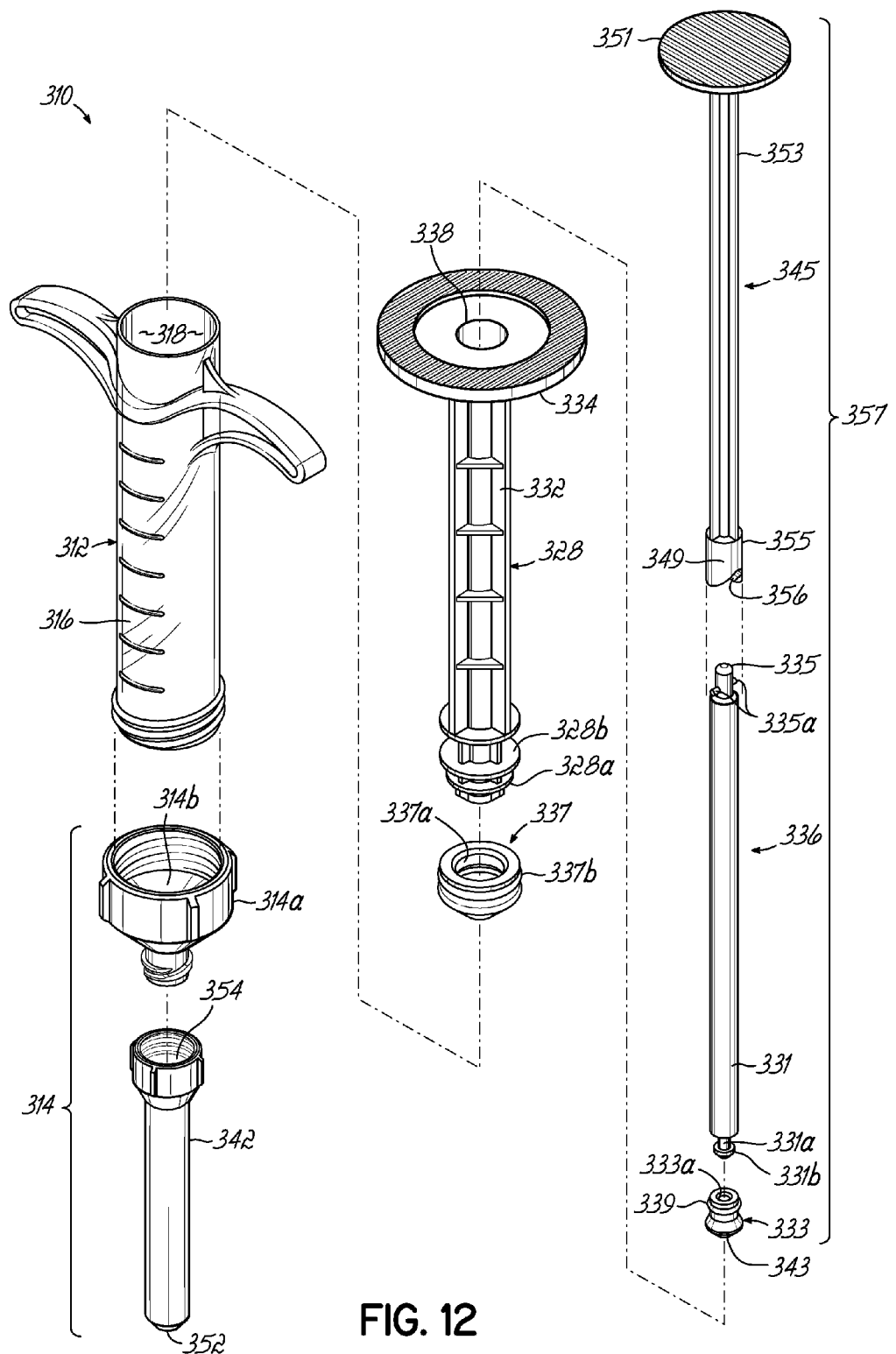
FIG. 12 is a further disassembled perspective view of the assembly of FIG. 11.
Figure 15:
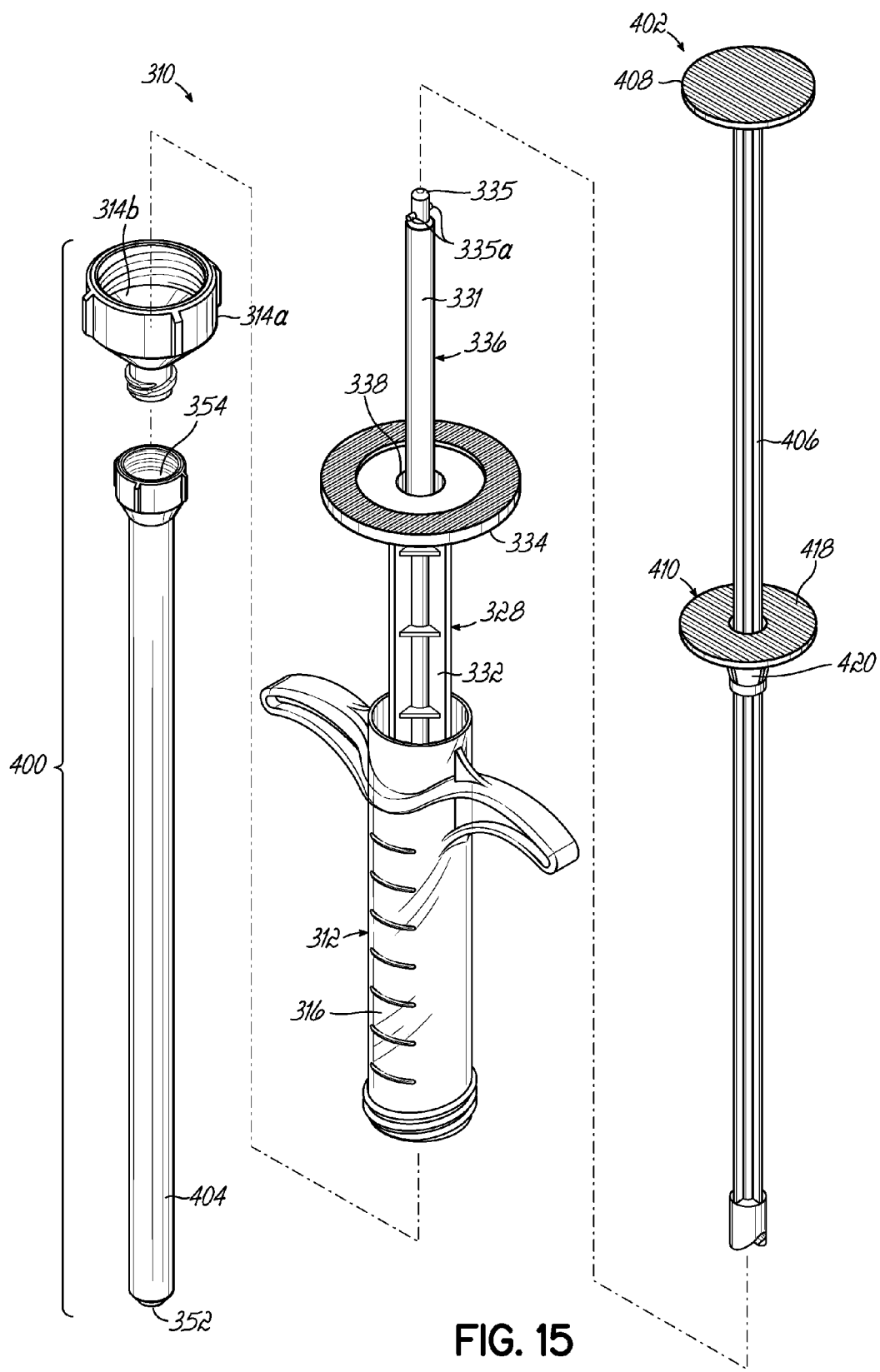
FIG. 15 is a disassembled perspective view showing components of the assembly of FIG. 11, but with an alternate cannulus device and an alternate extension device.
Figure 16A:
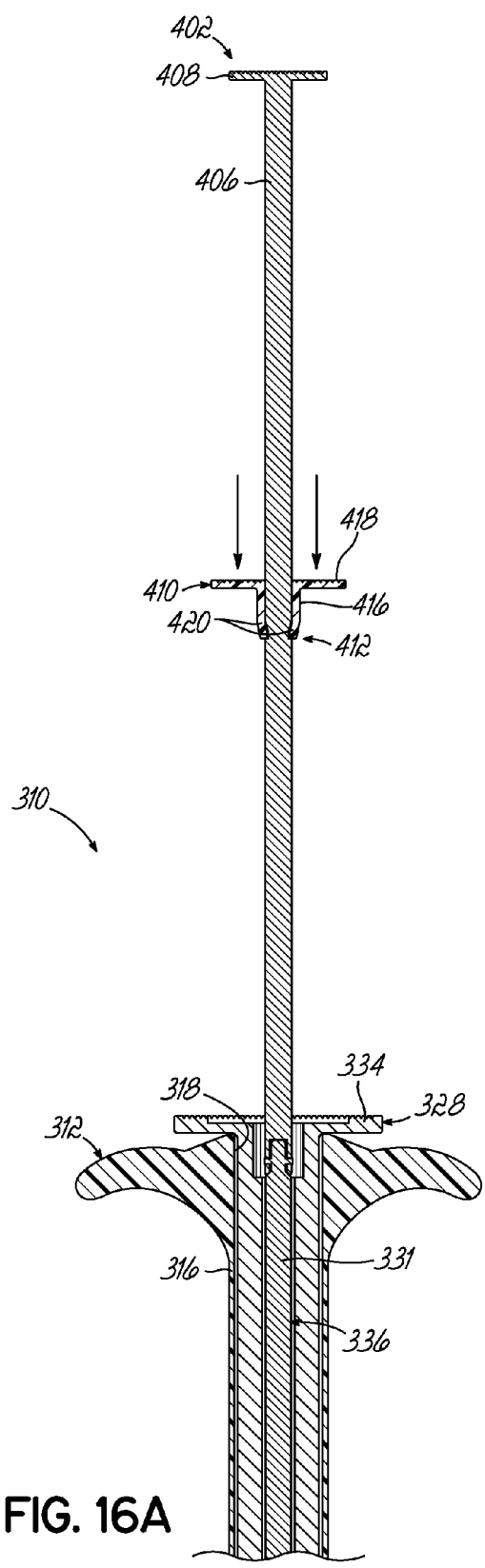
FIGS. 16A-16D are partial cross-sectional views showing bone graft material being dispensed from the dispensing syringe device and the cannulus device.
Figure 16B:
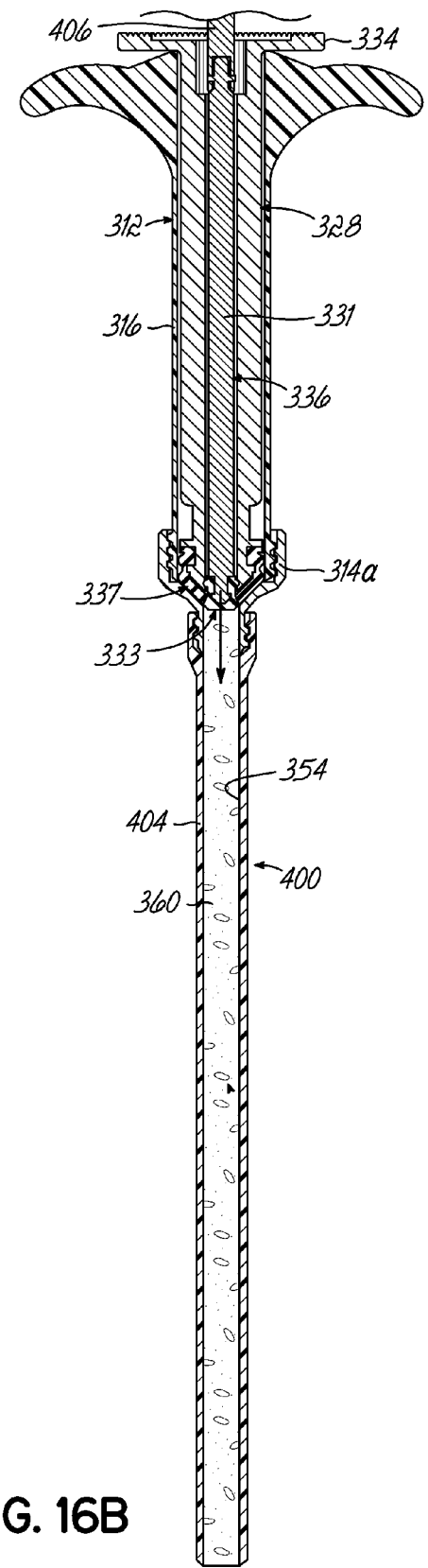
Figure 16C:
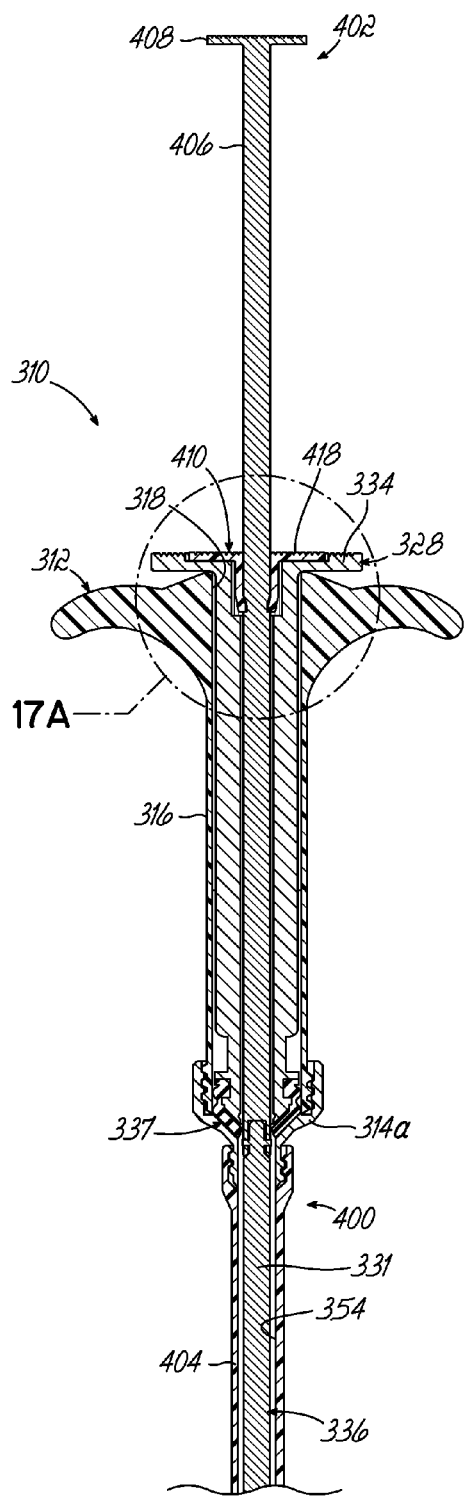
Figure 16D:
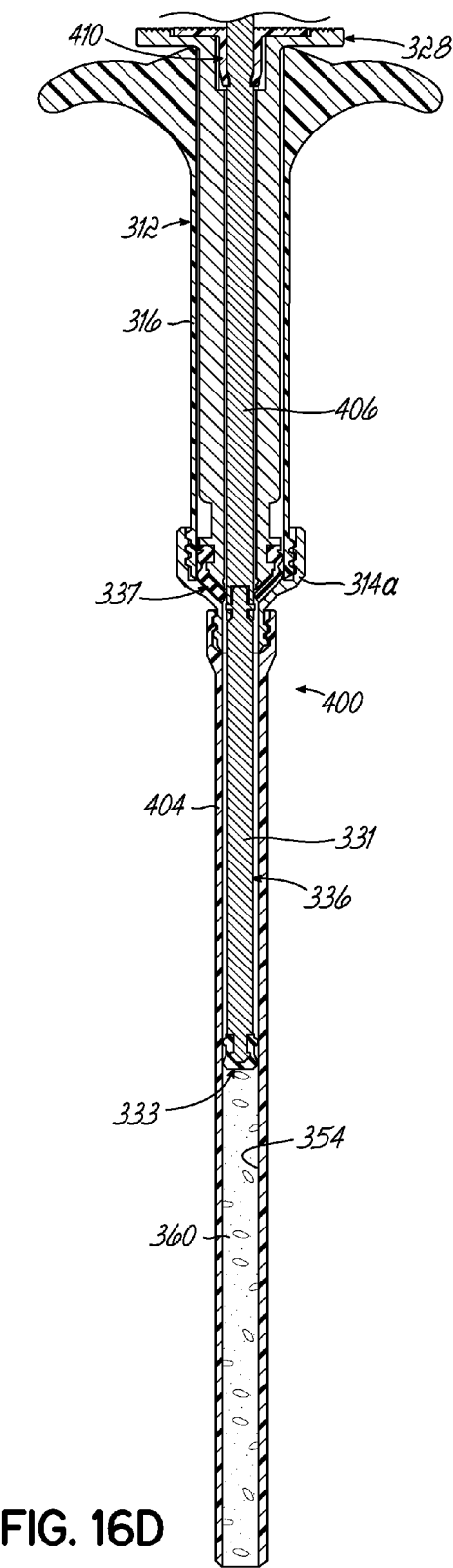

Because of the extended length of the body portion 404 of the cannulus device 400, the extension device 402 has a substantially longer shaft 406 than the shaft 353 of the extension device 345 (compare FIGS. 12 and 15). The extension device 402 includes a first finger ledge 408 connected with the shaft 406 near an end thereof. The first finger ledge 408 is generally similar to the finger ledge 351 described above, and provides a surface where a user can press on the extension device 402. The extension device 402 also includes a second finger ledge 410, which is useful because of the longer shaft 406. In particular, the second finger ledge 410 provides an additional surface where a user can press on the extension device 402.

The second finger ledge 410 is operatively associated with the shaft 406 in a manner that allows the second finger ledge 410 to transfer downward force to the shaft 406, but also allows the shaft 406 to be moved downwardly relative to the second finger ledge 410. In particular, the shaft 406 is allowed to move downwardly relative to the second finger ledge 410 once the second finger ledge 410 reaches the plunger base 334. To that end, the shaft 406 includes an indented region 412 that is generally medially-located along the length of the shaft 406. The indented region 412 forms a shelf 414.

The second finger ledge 410 includes a hub 416 that supports a radially-extending ledge surface 418. The hub 416 generally surrounds the shaft 406, and the ledge surface 418 provides a location where a user presses on the second finger ledge 410. The second finger ledge 410 also includes longitudinally-extending legs 420. The legs 420 are flexibly coupled with the hub 416, and also generally surround the shaft 406. The legs 420 are biased in a direction radially toward the shaft 406, but can be flexed radially outward.

The legs 420 and the shelf 414 are configured for operatively coupling the second finger ledge 410 with the shaft 406. In particular, the legs 420 are biased radially inwardly and follow the shape of the indented region 412. The legs 420 can engage the shelf 414. When the legs 420 engage the shelf 414, the second finger ledge 410 transfers downward force to the shaft 406, allowing a user to press on the ledge surface 418 to move the shaft 406 downwardly (FIGS. 16A-16D).

Figure 17A:
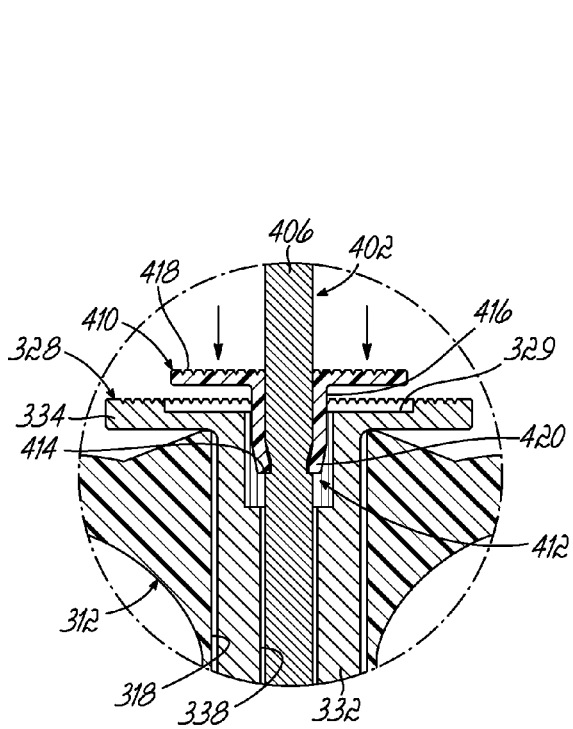
FIG. 17A is an enlarged view showing the circled region of FIG. 16C, and showing a second finger ledge near a plunger base of a plunger.
Figure 17B:
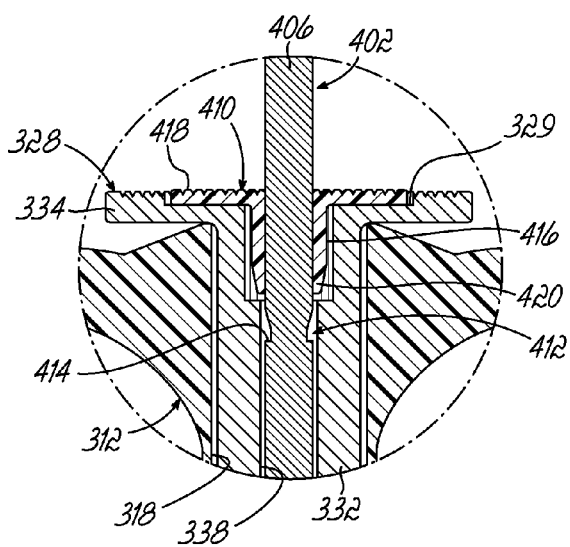
FIG. 17B is an enlarged view like FIG. 17A, but showing the second finger ledge received in a socket of the plunger, and a shaft of an extension device being moved downwardly relative to the second finger ledge.
Figure 17C:
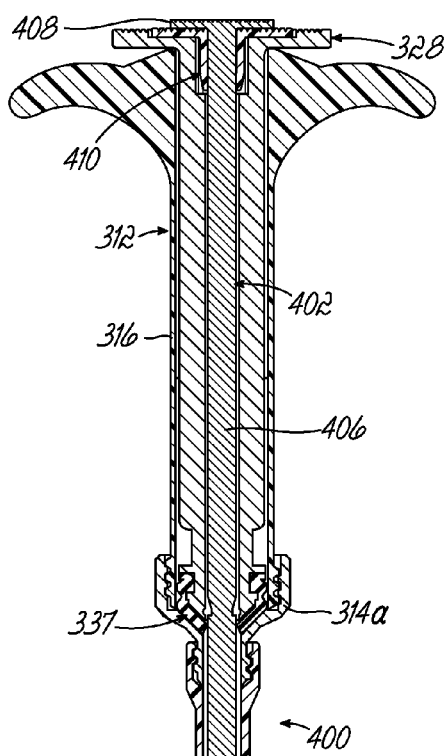
FIG. 17C is a cross-sectional view showing bone graft material being further dispensed from the dispensing syringe device and the cannulus device after the second finger ledge reaches the plunger base.

As the length of the shaft 406 is moved into the plunger 328, the second finger ledge 410 approaches the plunger base 334 (FIG. 17A). The second finger ledge 410 does not impede further downward movement of the shaft 406 when the second finger ledge 410 reaches the plunger base 334, however. When the second finger ledge 410 is moved to its downward-most position, a user presses on the first finger ledge 408, and the shaft 406 continues its downward movement. In particular, when the user presses on the first finger ledge 408 and the second finger ledge 410 can no longer move, the shaft 406 moves downwardly relative to the second finger ledge 410 (FIG. 17B). The legs 420 of the second finger ledge 410 flex radially outward, following the shape of the indented region 412 of the shaft 406. The legs 420 flex further radially outward and surround the shaft 406, but do not prevent the shaft 406 from moving further downwardly relative to the second finger ledge 410. Thereby, the full length of the shaft 406 can be moved downwardly for directing the bone graft material 360 out of the cannulus device 400.

Optionally, the plunger 328 can include a socket 329 for receiving the second finger ledge 410, as shown. When the second finger ledge 410 is received in the socket 329, the ledge surface 418 is generally co-planar with the plunger base 334 (FIG. 17B). The socket 329 is formed in the plunger body 332 and the plunger base 334. In a similar manner, the plunger 328 can include the socket 329 for receiving the finger ledge 351 of the extension device 345.

The extension device 402 with two finger ledges is useful for one-handed operation, such as where a user grips the syringe barrel 316 with his hand, and uses his thumb to operate the extension device 402. In particular, the user initially presses his thumb on the second finger ledge 410 to move the shaft 406 downwardly. When the second finger ledge 410 reaches the plunger base 334, the user then presses his thumb on the first finger ledge 408 to further move the shaft downwardly. Thereby, the user can operate even an extended-length extension device, such as the extension device 402, using only one hand.

Figure 18:
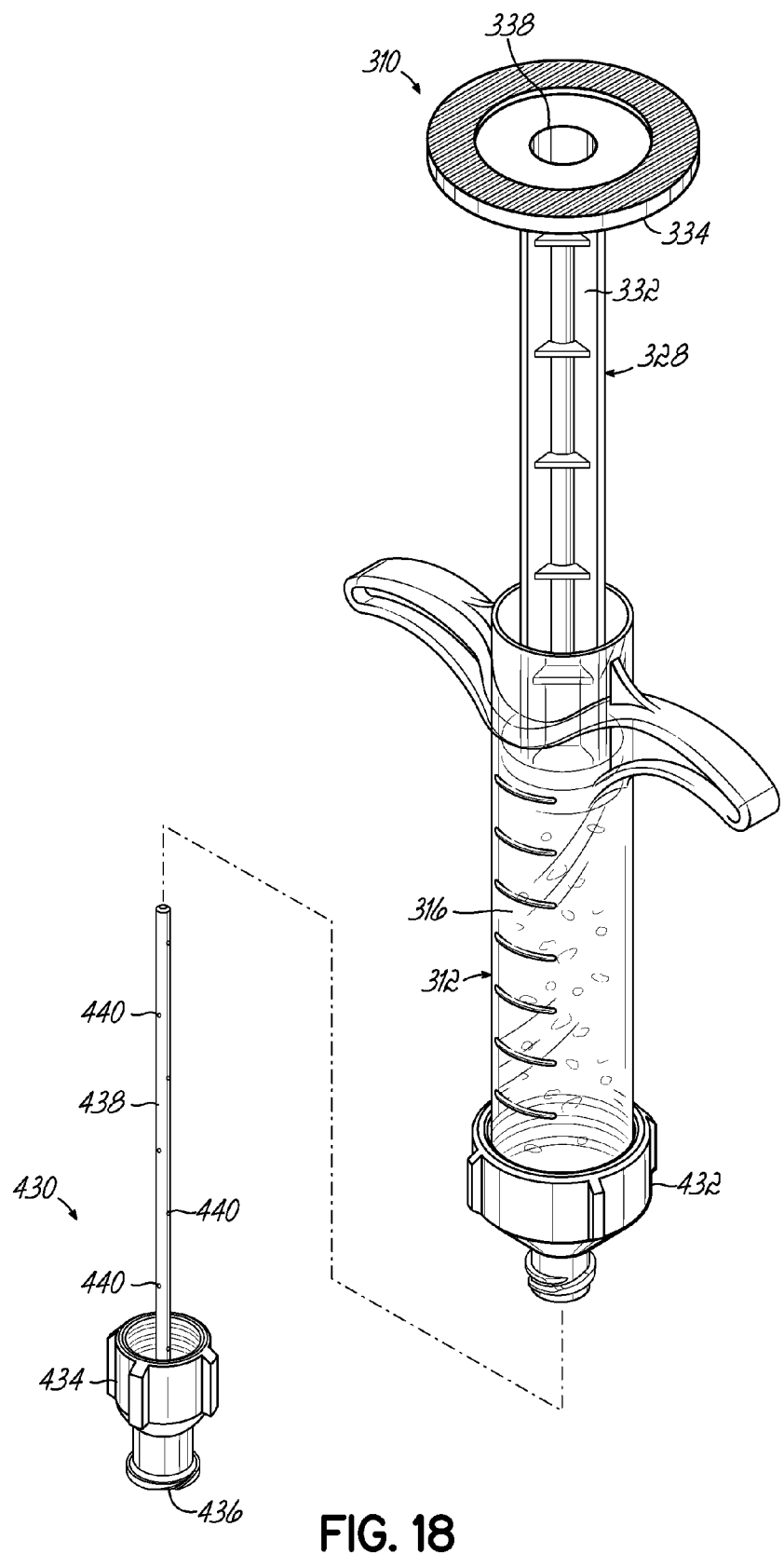
FIG. 18 is a disassembled perspective view showing components of the assembly of FIG. 11 with a hydration device.

Referring next to FIGS. 18-20, a hydration device 430 is shown that may be used with any of the assemblies 10, 110, 210, and 310. In the embodiment shown, the hydration device 430 is shown in conjunction with components of the assembly 310. The hydration device 430 is configured to be removably coupled with the syringe barrel 316 in order to add a fluid component to the bone graft material 360 contained in the syringe barrel 316. The hydration device 430 may include any of the structures shown in Application Ser. No. 61/837,315, which is incorporated by reference herein in its entirety.

In the embodiment shown, the hydration device 430 includes a syringe barrel connector 432 and a main body portion 434. The syringe barrel connector 432 is configured to be removably coupled with the syringe barrel 316, such as by using complementary threaded portions on the syringe barrel connector 432 and the syringe barrel 316, for example. The syringe barrel connector 432 may be generally similar to the attachment portion 314a of the cannulus device 314 described above. The main body portion 434 is configured to be removably coupled with the syringe barrel connector 432, such as by using complementary threaded portions on the main body portion 434 and the syringe barrel connector 432, for example. The main body portion 434 is also configured to be coupled with a fluid component source via a fluid inlet 436.

The hydration device 430 includes a tubular member 438 which is supported by the main body portion 434. The tubular member 438 is in fluid communication with the fluid inlet 436 for receiving a fluid component. The tubular member 438 includes a plurality of openings 440 that are disposed along the length of the tubular member 438.

When the hydration device 430 is coupled with the syringe barrel 316, the tubular member 438 extends within the syringe barrel 316 in such a manner that the bone graft material 360 generally surrounds the tubular member 438 (FIG. 19). A fluid component can be introduced through the fluid inlet 436 and into the tubular member 438. The fluid component can move from the tubular member 438 through the openings 440, thereby moving into the bone graft material 360.

In order to accommodate the additional volume of the fluid component in the syringe barrel, the plunger head 330 may include one or more vents that allow air in the bone graft material 360 to escape. In the embodiment shown, vents 333b are provided in the stopper element 333. Thereby, when the fluid component moves into the bone graft material 360, air displaced by the fluid component can escape through the vents 333b (FIG. 20).

Advantageously, the assemblies 10, 110, 210, and 310 can be used for dispensing other types of biomaterials than bone graft material. In addition, it will be appreciated that various of the features disclosed above in association with certain of the assemblies 10, 110, 210, and 310 might also be used with others of the assemblies 10, 110, 210, and 310.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. An assembly, comprising:
   a dispensing syringe device configured to receive and to dispense biomaterial, the dispensing syringe device including a syringe barrel for receiving the biomaterial, a discharge outlet for dispensing the biomaterial from the syringe barrel, and a plunger received in the syringe barrel, the plunger having a plunger body and a plunger passageway extending therethrough configured to receive a stylet;
   a cannulus device configured to be coupled with the dispensing syringe device, to receive biomaterial from the dispensing syringe device, and to dispense the biomaterial, the cannulus device including a cannulus passageway configured to receive the biomaterial and a dispensing opening configured to dispense the biomaterial;
   a plunger plug positioned in the plunger passageway of the plunger, the plunger plug including a shaft portion that extends from a first end to a second end; and
   an extension device that extends from a first end to a second end, wherein the first end of the shaft portion is configured to be releasably coupled to the second end of the extension device,
   wherein the extension device comprises a first finger ledge and a second finger ledge, the first and second finger ledges providing surfaces where a user can press on the extension device, and the second finger ledge is spaced from the first finger ledge along the extension device toward plunger plug.

2. The assembly of claim 1, further comprising a stylet configured to move in the plunger passageway and the cannulus passageway and to move the biomaterial in the cannulus passageway out of the dispensing opening.

3. The assembly of claim 1, wherein the shaft portion includes a threaded portion and the plunger body includes a threaded portion, the threaded portion of the shaft portion being configured to engage with the threaded portion of the plunger body to limit movement of the shaft portion relative to the plunger body.

4. The assembly of claim 1, wherein the shaft portion includes a rib and the plunger body includes a groove, the rib of the shaft portion being configured to engage with the groove of the plunger body to limit movement of the shaft portion relative to the plunger body.

5. The assembly of claim 1, wherein the plunger plug further comprises a stopper element coupled with the shaft portion, the stopper element being configured to move in the cannulus passageway and to move the biomaterial in the cannulus passageway out of the dispensing opening.

6. The assembly of claim 1, wherein the extension device comprises a shaft, wherein the second finger ledge is operatively associated with the shaft to allow the second finger ledge to transfer downward movement to the shaft and to allow the shaft to be moved downwardly relative to the second finger ledge.

7. The assembly of claim 1, wherein the cannulus passageway includes a radially-inwardly tapering region near the dispensing opening.

8. An assembly, comprising:
   a dispensing syringe device configured to receive and to dispense biomaterial, the dispensing syringe device including a syringe barrel for receiving the biomaterial, a discharge outlet for dispensing the biomaterial from the syringe barrel, and a plunger received in the syringe barrel, the plunger having a plunger body and a plunger passageway extending therethrough configured to receive a stylet;
   a cannulus device configured to be coupled with the dispensing syringe device, to receive biomaterial from the dispensing syringe device, and to dispense the biomaterial, the cannulus device including a cannulus passageway configured to receive the biomaterial and a dispensing opening configured to dispense the biomaterial;
   a plunger plug positioned in the plunger passageway of the plunger, the plunger plug including a shaft portion; and
   an extension device comprising a shaft, a first finger ledge and a second finger ledge,
   wherein the shaft portion is configured to be coupled to the extension device, and the second finger ledge is operatively associated with the shaft to allow the second finger ledge to transfer downward movement to the shaft and to allow the shaft to be moved downwardly relative to the second finger ledge.

9. The assembly of claim 8, wherein the shaft portion includes a rib and the plunger body includes a groove, the rib of the shaft portion being configured to engage with the groove of the plunger body to limit movement of the shaft portion relative to the plunger body.

10. The assembly of claim 8, wherein the plunger plug further comprises a stopper element coupled with the shaft portion, the stopper element being configured to move in the cannulus passageway and to move the biomaterial in the cannulus passageway out of the dispensing opening.

11. The assembly of claim 8, wherein the cannulus passageway includes a radially-inwardly tapering region near the dispensing opening.

* * * * *